(12) United States Patent
Williams et al.

(10) Patent No.: US 10,905,861 B2
(45) Date of Patent: Feb. 2, 2021

(54) MATRIX SUPPORTED BALLOON ARTICULATION SYSTEMS, DEVICES, AND METHODS FOR CATHETERS AND OTHER USES

(71) Applicant: Project Moray, Inc., Belmont, CA (US)

(72) Inventors: Timothy H. Williams, Palo Alto, CA (US); Keith Phillip Laby, Oakland, CA (US); Mark D. Barrish, Belmont, CA (US)

(73) Assignee: Project Moray, Inc., Belmont, CA (US)

( * ) Notice: Subject to any disclaimer, the term of this patent is extended or adjusted under 35 U.S.C. 154(b) by 190 days.

(21) Appl. No.: 15/961,369

(22) Filed: Apr. 24, 2018

(65) Prior Publication Data

US 2019/0117942 A1    Apr. 25, 2019

Related U.S. Application Data

(60) Provisional application No. 62/489,864, filed on Apr. 25, 2017.

(51) Int. Cl.
*A61M 25/10*     (2013.01)
*A61M 25/01*     (2006.01)
(Continued)

(52) U.S. Cl.
CPC ....... *A61M 25/1011* (2013.01); *A61B 17/068* (2013.01); *A61F 2/958* (2013.01);
(Continued)

(58) Field of Classification Search
CPC ............ A61M 25/1011; A61M 25/009; A61M 25/005; A61M 25/0136; A61M 25/0155;
(Continued)

(56) References Cited

U.S. PATENT DOCUMENTS 3,284,964 A    11/1966   Saito
3,459,221 A     8/1969   Axelrod
(Continued)

FOREIGN PATENT DOCUMENTS

CN    107835703    3/2018
CN    107835704    3/2018
(Continued)

OTHER PUBLICATIONS

Approppedia.org, "3-D Printing of Electrically Conductive Materials Literature Review", Appropedia: The sustainability Wiki, by Michigan Tech's Open Sustainability Technology Lab, Jul. 13, 2016, 9 pages.
(Continued)

*Primary Examiner* — Tiffany Legette
(74) *Attorney, Agent, or Firm* — Kilpatrick Townsend & Stockton LLP

(57) ABSTRACT

Articulation devices, systems, methods for articulation, and methods for fabricating articulation structures make use of balloon arrays, with inflation of the balloons locally altering articulation. Inflation fluid may be directed toward the balloons from an inflation fluid source via a series of channels, the balloons and channels included in a helical multi-balloon assembly. The balloons may be supported by encasing the helical balloon assembly in a polymer matrix, such as by winding the balloon assembly onto a mandrel and dip-coating some or all of the assembly in an elastomer such as a silicone, a urethane, or the like. The balloons may be supported by one or more spring, with loops of the spring(s) optionally being inward of the balloons, outward of the balloons, or interspersed between the balloons, and/or a mesh tube, braid, or other compliant materials may be included. Articulation balloon arrays may be disposed in an annular space bordered by inner and outer tubular sheaths,
(Continued)

with a portion of one or both sheaths being axially slidable relative to the balloons so as to facilitate elongation and bending.

18 Claims, 12 Drawing Sheets

(51) Int. Cl.
| | |
|---|---|
| *B25J 9/14* | (2006.01) |
| *A61B 17/068* | (2006.01) |
| *B25J 9/06* | (2006.01) |
| *A61M 25/00* | (2006.01) |
| *B25J 19/06* | (2006.01) |
| *A61F 2/958* | (2013.01) |
| *A61B 17/00* | (2006.01) |
| *A61B 1/008* | (2006.01) |

(52) U.S. Cl.
CPC ...... *A61M 25/005* (2013.01); *A61M 25/0009* (2013.01); *A61M 25/0136* (2013.01); *A61M 25/0155* (2013.01); *A61M 25/1002* (2013.01); *B25J 9/06* (2013.01); *B25J 9/142* (2013.01); *B25J 19/068* (2013.01); *A61B 1/008* (2013.01); *A61B 2017/00243* (2013.01); *A61B 2017/00305* (2013.01); *A61B 2017/00318* (2013.01); *A61B 2017/00557* (2013.01); *A61B 2017/00853* (2013.01); *A61M 25/1027* (2013.01)

(58) Field of Classification Search
CPC ............ A61M 25/1027; A61M 25/1002; B25J 19/068; B25J 19/06; A61B 2017/00243; A61B 2017/00305; A61B 2017/00318; A61B 2017/00557; A61B 2017/00853; A61B 1/008
See application file for complete search history.

(56) References Cited

U.S. PATENT DOCUMENTS

| | | | |
|---|---|---|---|
| 3,523,547 A | 8/1970 | Hatch, Jr. et al. | |
| 3,915,194 A | 10/1975 | Friedrich | |
| 3,934,605 A | 1/1976 | Legris | |
| 4,082,324 A | 4/1978 | Obrecht | |
| 4,230,143 A | 10/1980 | Dettmann et al. | |
| 4,494,417 A | 1/1985 | Larson et al. | |
| 4,762,130 A | 8/1988 | Fogarty et al. | |
| 4,784,042 A | 11/1988 | Paynter | |
| 4,794,912 A | 1/1989 | Lia | |
| 4,838,859 A | 6/1989 | Strassmann | |
| 4,890,611 A | 1/1990 | Monfort et al. | |
| 4,893,613 A | 1/1990 | Hake | |
| 4,900,218 A | 2/1990 | Sutherland | |
| 4,983,165 A | 1/1991 | Loiterman | |
| 5,018,506 A | 5/1991 | Danna et al. | |
| 5,304,132 A | 4/1994 | Jang | |
| 5,308,356 A | 5/1994 | Blackshear, Jr. et al. | |
| 5,337,733 A | 8/1994 | Bauerfeind et al. | |
| 5,413,107 A | 5/1995 | Oakley et al. | |
| 5,469,756 A | 11/1995 | Feiten | |
| 5,489,270 A | 2/1996 | Van Erp | |
| 5,501,667 A | 3/1996 | Verduin, Jr. | |
| 5,529,088 A | 6/1996 | Asou | |
| 5,619,993 A | 4/1997 | Lee | |
| 5,820,595 A | 10/1998 | Parodi | |
| 5,823,955 A | 10/1998 | Kuck et al. | |
| 5,865,801 A | 2/1999 | Houser | |
| 6,066,125 A | 5/2000 | Webster, Jr. | |
| 6,146,339 A | 11/2000 | Biagtan et al. | |
| 6,178,872 B1 | 1/2001 | Schulz | |
| 6,503,194 B2 | 1/2003 | Pauker | |
| 6,520,933 B1 | 2/2003 | Evans et al. | |
| 6,527,739 B1 | 3/2003 | Bigus et al. | |
| 6,648,879 B2 | 11/2003 | Joye et al. | |
| 6,811,550 B2 | 11/2004 | Holland et al. | |
| 6,875,170 B2 | 4/2005 | Francois et al. | |
| 6,928,313 B2 | 8/2005 | Peterson | |
| 6,951,226 B2 | 10/2005 | Eriksson et al. | |
| 7,060,062 B2 | 6/2006 | Joye et al. | |
| 7,090,637 B2 | 8/2006 | Danitz et al. | |
| 7,373,955 B2 | 5/2008 | Steinberg | |
| 7,422,579 B2 | 9/2008 | Wahr et al. | |
| 7,570,981 B2 | 8/2009 | Peterson | |
| 7,578,787 B2 | 8/2009 | Boese et al. | |
| 7,780,723 B2 | 8/2010 | Taylor | |
| 7,824,391 B2 | 11/2010 | Gesswein | |
| 7,850,683 B2 | 12/2010 | Elkins et al. | |
| 7,879,004 B2 | 2/2011 | Seibel et al. | |
| 7,957,790 B2 | 6/2011 | Kleen | |
| 7,963,911 B2 | 6/2011 | Turliuc | |
| 8,125,755 B2 | 2/2012 | Garcia et al. | |
| 8,201,473 B2 | 6/2012 | Knoll | |
| 8,372,055 B2 | 2/2013 | Thornton et al. | |
| 8,388,520 B2 | 3/2013 | Stefanchik et al. | |
| 8,398,540 B2 | 3/2013 | Hassidov et al. | |
| 8,423,115 B2 | 4/2013 | Koblish et al. | |
| 8,469,059 B1 | 6/2013 | Forst | |
| 8,764,725 B2 | 7/2014 | Averbuch | |
| 8,784,476 B2 | 7/2014 | Caro et al. | |
| 8,845,523 B2 | 9/2014 | Lawrence et al. | |
| 8,863,608 B2 | 10/2014 | Fischer et al. | |
| 2001/0007070 A1 | 7/2001 | Stewart et al. | |
| 2002/0045929 A1 | 4/2002 | Diaz | |
| 2002/0049408 A1 | 4/2002 | Van Moorlegem et al. | |
| 2002/0058951 A1 | 5/2002 | Fiedler | |
| 2003/0069475 A1 | 4/2003 | Banik et al. | |
| 2006/0058598 A1 | 3/2006 | Esposito | |
| 2006/0084964 A1 | 4/2006 | Knudson et al. | |
| 2006/0235368 A1 | 10/2006 | Oz | |
| 2007/0060997 A1 | 3/2007 | de Boer | |
| 2007/0100235 A1 | 5/2007 | Kennedy, II | |
| 2007/0123925 A1 | 5/2007 | Benjamin et al. | |
| 2007/0169761 A1 | 7/2007 | Price | |
| 2007/0270686 A1 | 11/2007 | Ritter et al. | |
| 2007/0288095 A1 | 12/2007 | Wirtel et al. | |
| 2008/0091073 A1 | 4/2008 | Park et al. | |
| 2008/0215008 A1 | 9/2008 | Nance et al. | |
| 2009/0076584 A1 | 3/2009 | Mao et al. | |
| 2009/0105816 A1 | 4/2009 | Olsen et al. | |
| 2009/0112159 A1 | 4/2009 | Slattery et al. | |
| 2009/0281523 A1 | 11/2009 | Sacco et al. | |
| 2010/0168665 A1 | 7/2010 | Skerven | |
| 2011/0112632 A1 | 5/2011 | Chau et al. | |
| 2011/0270126 A1 | 11/2011 | Gunday et al. | |
| 2011/0295181 A1* | 12/2011 | Dann | A61M 1/3655 604/8 |
| 2011/0295247 A1 | 12/2011 | Schlesinger et al. | |
| 2011/0295248 A1 | 12/2011 | Wallace et al. | |
| 2012/0271319 A1 | 10/2012 | Bromander et al. | |
| 2012/0310227 A1 | 12/2012 | Katou | |
| 2013/0091974 A1 | 4/2013 | Riwan et al. | |
| 2013/0096377 A1 | 4/2013 | Duindam et al. | |
| 2013/0103019 A1 | 4/2013 | Joye et al. | |
| 2013/0178838 A1 | 7/2013 | Malkowski et al. | |
| 2013/0296983 A1 | 11/2013 | Keller et al. | |
| 2014/0062405 A1 | 3/2014 | Videbaek | |
| 2014/0142666 A1 | 5/2014 | Phelan et al. | |
| 2014/0243688 A1 | 8/2014 | Caron et al. | |
| 2014/0249506 A1 | 9/2014 | Laduca | |
| 2014/0276933 A1 | 9/2014 | Hart et al. | |
| 2014/0276934 A1 | 9/2014 | Balaji et al. | |
| 2015/0182728 A1* | 7/2015 | Khalaj | A61M 25/02 604/180 |
| 2015/0209558 A1 | 7/2015 | Charlebois et al. | |
| 2015/0265807 A1 | 9/2015 | Park et al. | |
| 2016/0128767 A1 | 5/2016 | Azamian et al. | |
| 2016/0279388 A1* | 9/2016 | Barrish | A61B 34/20 |
| 2017/0021132 A1 | 1/2017 | Laby et al. | |
| 2017/0021143 A1 | 1/2017 | Barrish et al. | |
| 2017/0157361 A1 | 6/2017 | Barrish et al. | |

(56) References Cited

U.S. PATENT DOCUMENTS

| | | | |
|---|---|---|---|
| 2017/0157363 | A1 | 6/2017 | Barrish et al. |
| 2018/0071492 | A1 | 3/2018 | Laby et al. |
| 2018/0085559 | A1 | 3/2018 | Laby et al. |
| 2018/0200483 | A1 | 7/2018 | Laby et al. |

FOREIGN PATENT DOCUMENTS

| | | |
|---|---|---|
| CN | 107921236 | 4/2018 |
| EP | 3274038 | 1/2018 |
| EP | 3274039 | 1/2018 |
| EP | 3274040 | 1/2018 |
| WO | 2007053625 | 5/2007 |
| WO | 2014128507 | 8/2014 |

OTHER PUBLICATIONS

Arsalan et al., "Comparison of Current Costs and Reimbursement for Transcatheter and Surgical Aortic Valve Replacement", J. Am. Coll. Cardiol., vol. 67, No. 13, ACC.i2 Interventional Cardiology, Available online at http://content.onlinejacc.org/article.aspxarticleid=2508037, Apr. 5, 2016; 2 pages.

Atzori et al., "Indoor Navigation System Using Image and Sensor Data Processing on a Smartphone", Optimization of Electrical and Electronic Equipment (OPTIM), 2012 13th International Conference, Available online at https://www.researchgate.net/publication/261267019_Indoor_navigation_system_using_image_and_sensor_data_processing_on_a_smartphone, May 24-26, 2012, pp. 1158-1163.

Au et al., "Microvalves and Micropumps for BioMEMS", Micromachines, vol. 2, ISSN 2072-666X, Available online at www.mdpi.com/journal/micromachines, 2011, pp. 179-220.

Backer et al., "Percutaneous Transcatheter Mitral Valve Replacement", Circulation: Cardiovascular Interventions, Available online at http://circinterventions.ahajournals.org/content/7/3/400.full, 2014, pp. 400-409.

Bar-Cohen, "WorldWide ElectroActive Polymers", EAP (Artificial Muscles) Newsletter, vol. 16, No. 1, (The 31th issue), Available online at http://eap.jpl.nasa.gov, Jun. 2014, pp. 1-18.

BBC News Science & Environment, "Nanotube Yarns Twist Like Muscles", BBC News, Available online at http://www.bbc.co.uk/news/science-environment-15287185, Oct. 14, 2011, 8 pages.

Beahm et al., "Catheter Bonding Technology Overview", Avaialble online at www.beahmdesigns.com, Apr. 2012, 4 pages.

Biswal et al., "Development of an Active Catheter Mechanism Using IPMC for in Vivo Inspection", Journal of Mechatronics and Automation vol. 1, No. 1, Available online at: http://www.academia.edu/10757534/Development_of_an_Active_Catheter_Mechanism_using_IPMC_for_in_vivo_Inspection, 2014, 10 pages.

Bolling, "Can We Predict Mitral Valve Repair Rates by Individual Surgeons' Mitral Volume", Tex Heart Inst J., vol. 38, No. 6, 8th Current Trends in Aortic and Cardiothoracic Surgery, Available online at http://www.ncbi.nlm.nih.gov/pmc/articles/PMC3233323/, 2011, pp. 703-704.

Buntz, "Forget IoT: The Internet of Moving Things Is Where It Is at", Qmed, Available online at http://www.qmed.com/mpmn/medtechpulse/forget-iot-internet-moving-things-where-it, Dec. 10, 2014, 3 pages.

Buntz, "Graphene Breakthrough Could Be a Boon to Flexible Electronics", Electronic Components, Qmed, Available online at http://www.qmed.com/mpmn/medtechpulse/graphene-breakthrough-could-be-boon-flexible-electronicscid=nl.qmed02, Nov. 14, 2013, 1 page.

Buntz, "How Tiny Artificial Muscles Could Be Huge Energy Savers", Motion Control, Qmed, Available online at http://www.qmed.com/mpmn/medtechpulse/how-tiny-artificial-muscles-could-be-huge-energy-saverscid=nl.qmed02.20150223, Feb. 20, 2015, 3 pages.

Buntz, "Using a T-Shirt Printer to Make Medical Circuits", Qmed, Electronic Components, Available online at http://www.qmed.com/mpmn/medtechpulse/using-t-shirt-printer-make-medical-circuits, Nov. 17, 2014, 3 pages.

Catherine et al., "Comparative Review of Endoscopic Devices Articulations Technologies Developed for Minimally Invasive Medical Procedures", Applied Bionics and Biomechanics, vol. 8, 2011, pp. 151-171.

Chakraborty et al., "Mems Micro-Valve for Space Applications", Sensors and Actuators A: Physical, vol. 83, No. 1-3, 2000, pp. 188-193.

Chandgadkar, "An Indoor Navigation System for Smartphones", Available online at http://www.doc.ic.ac.uk/teaching/distinguished-projects/2013/a.chandgadkar.pdf, Jun. 18, 2013, 80 pages.

Chang et al., "Electrostatically-Actuated Reconfigurable Elastomer Microfluidics", Available online at http://people.eecs.berkeley.edu/~maharbiz/HH_paper_mpchang_0008.pdf, 4 pages.

Chen et al., "High-Pressure On-Chip Mechanical Valves for Thermoplastic Microfluidic Devices", The Royal Society of Chemistry, Lab Chip, vol. 9, 2009. pp. 3511-3516.

Clippard New!, "New 7 mm Electronic Valves". Available online at http://www.clippard.com/products/electronic-valve-7mm, 2 pages.

Conrad et al., "Closed Loop Task Space Control of an Interleaved Continuum-Rigid Manipulator", IEEE International Conference on Robotics and Automation, Available online at http://robotics.engr.wisc.edu/cgi-bin/wikiwp/category/continuum-robotics/, 2015, 8 pages.

Corma Inc., "Corrugators and Pulsating Corrugators", Available online at http://corma.com/products/corrugators-pulsating-corrugators/, 2011, 3 pages.

Coyne, "Comprehensive Manufacturing of Microfluidic Diagnostic Devices", IVD, MDDI Medical Device and Diagnostic Industry, Jun. 17, 2014, 4 pages.

Creganna Tactx Medical, "Deflectable and Steerable Catheter Handbook". Terminology Guide & Design Options, Available online at http://www.creganna.com/wp-content/uploads/SteeringandDeflectionTerminologyrev3.pdf, 7 pages.

Dabove et al., "Inertial Sensors for Smartphones Navigation", SpringerPlus, vol. 4, No. 834, Available online at http://www.ncbi.nlm.nih.gov/pmc/articles/PMC4695469/, 2015, 18 pages.

D'Arcy et al., "Valvular Heart Disease: The Next Cardiac Epidemic", vol. 97, No. 2, Available online at http://heart.bmj.com/content/97/2/91.extract, 2011, pp. 91-93.

De Sars et al., "A Practical Approach to the Design and Control of Active Endoscopes", Mechatronics, vol. 20, Available online at http://www.elsevierscitech.com/pdfs/Mechatronics_DeSars.pdf, 2010, pp. 251-264.

DMQ Inc., "Product Datasheet: silQflo™ Silicon Servo Valve", Available online at http://www.dmq-us.com/wp-content/uploads/2015/02/SSV-Datasheet-Rev-1.001.pdf, 2 pages.

Don et al., "Novel Velocity Model to Improve Indoor Localization Using Inertial Navigation With Sensors on a Smart Phone", Avaialble online at http://arxiv.org/pdf/1601.03004.pdf, Jan. 12, 2016, 5 pages.

Dupont et al., "Snakes, Worms and Catheters: Continuum and Serpentine Robots for Minimally Invasive Surgery", IEEE ICRA Full Day Workshop, May 3, 2010, 60 pages.

Eitel, "The Rise of Soft Robots and the Actuators that Drive Them", Available online at http://machinedesign.com/robotics/rise-soft-robots-and-actuators-drive-them, Sep. 12, 2013, 7 pages.

Elveflow Plug & Play, "Microfluidics and Microfluidic Devices: A Review", Available online at http://www.elveflow.com/microfluidic-tutorials/microfluidic-reviews-and-tutorials/microfluidics-and-microfluidic-device-a-review/, 2015, 10 pages.

EP Vantage Ltd., "Edwards Tightens Transcatheter Valve Stranglehold", Available online at http://www.epvantage.com/Universal/View.aspxtype=Story&id=580885&isEPVantage=yes, Jun. 18, 2015, 2 pages.

Eucog Wiki, "Compliant Robots", Available online at http://www.eucognition.org/eucog-wiki/Compliant_robots, 2012, 5 pages.

Fedak et al., "Evolving Concepts and Technologies in Mitral Valve Repair", American Heart Association, Inc., Contemporary Reviews in Cardiovascular Medicine, vol. 117, No. 7, Available online at http://circ.ahajournals.org/content/117/7/963.full, Feb. 19, 2008, pp. 963-974.

(56) References Cited

OTHER PUBLICATIONS

Festo AG & Co. KG, "Systematic Expertise Through Continuous Further Development", Bionic Handling Assistant, Available online at https://www.festo.com/net/supportportal/files/42050/brosch_fc_bha_3_0_en_lo.pdf, Apr. 2012, 6 pages.

Fite et al., "A Gas-Actuated Anthropomorphic Prosthesis for Transhumeral Amputees", IEEE Transactions on Robotics, vol. 24, No. 1, Feb. 2008, pp. 159-169.

Flexpoint Sensor Systems, Inc., "The Benefits of Using Bend Sensors", Sensor Products Inc., Available online at www.sensorprod.com, 2 pages.

Fornell, "Transcatheter Mitral Valve Replacement Devices in Development", Diagnostic and Interventional Cardiology, Available online at http://www.dicardiology.com/article/transcatheter-mitral-valve-replacement-devices-development, Dec. 30, 2014, 5 pages.

Fu et al., "Research on the Axis Shape of an Active Catheter", Int. J. Med. Robot.; vol. 4, No. 1, Mar. 2008, pp. 69-76.

Fu et al., "Steerable Catheters in Minimally Invasive Vascular Surgery", Int. J. Med. Robot., vol. 5, No. 4, Dec. 2009, pp. 381-391.

Gionata et al., "An Inertial and Qr Code Landmarks-Based Navigation System for Impaired Wheelchair Users", Available online at https://www.researchgate.net/publication/261551014_An_inertial_and_QR_code_landmarks-based_navigation_system_for_impaired_wheelchair users, May 29, 2014, pp. 205-214.

Grube, "Development of a TMVR Device Challenge to Innovators", ICI meeting, Dec. 13-15, 2015, 30 pages.

Haga et al., "Active Bending Catheter and Endoscope Using Shape Memory Alloy Actuators", Available online at www.intechopen.com, Shape Memory Alloys, 2010, 21 pages.

Haga et al., "Multi-Functional Active Catheter", Available online at http://bdml.stanford.edu/twiki/pub/Haptics/DesignReferencesSummer2009/MultifunctionalActiveCatheter.pdf, pp. 147-186.

Herrmann et al., "Novel Transcatheter Approaches", Heart Valve Summit, American association of Thoracic surgery, Available online at http://aats.org/multimedia/files/valve/2015/Presentations/Thursday/600-Herrmann.pdf, 2015, 26 pages.

Ikeuchi et al., "Development of Pressure-Driven Micro Active Catheter using Membrane Micro Emboss Following Excimer Laser Ablation (MeME-X) Process", IEEE International Conference on Robotics and Automation, Available online at http://ir.nul.nagoya-u.ac.jp/jspui/bitstream/2237/13924/1/ICRA09_MeMEX.pdf, May 12-17, 2009, pp. 4469-4472.

Jagadeesan, "Design and Control of an Active Catheter", Available online at http://scholar.harvard.edu/jayender/activecatheter, Jul. 14, 2016, 2 pages.

Jia et al., "Online Camera-Gyroscope Auto-Calibration for Cell-phones", IEEE Transactions on Image Processing, Available online at http://users.ece.utexas.edu/~bevans/papers/2015/autocalibration/autocalibrationIEEETransImageProcPaperDraft.pdf, 2013, 11 pages.

John Muir Health, "U.S. Aortic Stenosis Disease Prevalence and Treatment Statistics", Facts and Figures, Available Online at https://www.johnmuirhealth.com/services/cardiovascular-services/intervention/transcatheter-aortic-valve-replacement/facts-and-figures.html, 2016, 3 pages.

Johnson, "Modeling of Frictional Gas Flow in a Piezoelectrically Actuated High-pressure Microvalve for Flowrate Control", Dec. 16, 2005, 197 pages.

Jung et al., "A Modeling Approach for Continuum Robotic Manipulators: Effects of Nonlinear Internal Device Friction", IEEE/RSJ International Conference on Intelligent Robots and Systems, Sep. 25-30, 2011, pp. 5139-5146.

Kasahara et al., "Surface Modification of Polyethylene Terephthalate (PET) by 172-nm Excimer lamp", Technical paper, 2012, pp. 47-54.

Kato et al., "An Inchworm Type In-Pipe Mobile Microrobot Driven by Three Gas-liquid Phase-change Actuators", Proceedings of the Annual Meeting—American Society for Precision Engineering, 2003, pp. 295-298.

Kim et al., "Materials for Multifunctional Balloon Catheters with Capabilities in Cardiac Electrophysiological Mapping and Ablation Therapy", Nat Mater., vol. 10, No. 4, Available online at http://www.ncbi.nlm.nih.gov/pmc/articles/PMC3132573/, Apr. 2011, pp. 316-323.

Kirby et al., "Microfluidic Routing of Aqueous and Organic Flows at High Pressures: Fabrication and Characterization of Integrated Polymer Microvalve Elements", The Royal Society of Chemistry, Lab Chip, vol. 5, 2005, pp. 184-190.

Korane, "Robot Imitates an Elephant's Trunk", Available online at http://machinedesign.com/robotics/robot-imitates-elephant-s-trunk, Sep. 13, 2010, 5 pages.

Labsmith, Inc., "LabSmith uProcess™ System", LabSmith, Inc., Microfluidic Automation, Available online at http://www.labsmith.com/products/LabSmith_uProcess_Brochure.pdf_ga=1.142274551.472763250.1458083262., 2015, 6 pages.

Langelaar et al., "Modeling of a Shape Memory Alloy Active Catheter", 45th AIAA/ASME/ASCE/AHS/ASC Structures, Structural Dynamics & Materials Conference, American Institute of Aeronautics and Astronautics, Available online at http://citeseerx.ist.psu.edu/viewdoc/download?doi=10.1.1.125.1080&rep=rep1&type=pdf, Apr. 19-22, 2004, 16 pages.

Lee et al., "Fabrication, Characterization, and Computational Modeling of a Piezoelectrically Actuated Microvalve for Liquid Flow Control", Journal of Microelectromechanical Systems, vol. 15, No. 3, IEEE, Jun. 2006, pp. 686-696.

Levy, "Tiny Ultrasound Camera Images Blood Vessel Interior in 3-D", Medical Imaging, Qmed, Available online at http://www.qmed.com/mpmn/medtechpulse/tiny-ultrasound-camera-images-blood-vessel-interior-3-dcid=nl.qmed02, Mar. 3, 2014, 5 pages.

Maglione et al., "Ultra-High-Pressure Balloon Angioplasty for Treatment of Resistant Stenoses Within or Adjacent to Previously Implanted Pulmonary Arterial Stents", Circulation: Cardiovascular Interventions, Available online at http://circinterventions.ahajournals.org/content/2/1/52.full, 2009, pp. 52-58.

Malek et al., "Femtosecond Laser Machining and Lamination for Large-Area Flexible Organic Microfluidic Chips", European Physical Journal: Applied Physics, EDP Sciences, Available online at https://hal.archives-ouvertes.fr/hal-00480155/document, Apr. 2009, 8 pages.

Mazzarese, "Low-Profile Balloon Catheters are Critical to TAVR's Success", Medical Tubing Types by MDDI Staff, Available online at http://www.mddionline.com/article/low-profile-balloon-catheters-are-critical-tavr-success-10-21-2014cid=nl.mddi01.20141023, Oct. 21, 2014, 3 pages.

MDDI, Medical Plastics, "The Effect of Extrusion and Blow Molding Parameters on Angioplasty Balloon Production", Available online at http://www.mddionline.com/article/effect-extrusion-and-blow-molding-parameters-angioplasty-balloon-production, May 1, 1998, 4 pages.

Medtronic, "CoreValve™ System", Transcatheter Aortic Valve Delivery Catheter System Compression Loading System, 2014, 61 pages.

Messenger, "A Comprehensive Guide to the U.S. TAVR Market: Surveying the Field", Available online at http://www.meddeviceonline.com/doc/a-comprehensive-guide-to-the-u-s-tavr-market-surveying-the-field-0001, Apr. 12, 2016, 7 pages.

Mohty et al., "Valvular Heart Disease in Elderly Adults", Available online at http://www.uptodate.com/contents/valvular-heart-disease-in-elderly-adults, 2016, 6 pages.

Mount Sinai Hospital, "Researchers Compare Two-Year Clinical Outcomes of Mitral Valve Replacement and Repair in Treating Severe Valve Regurgitation", Icahn School of Medicine at Mount Sinai, Available online at http://www.mountsinai.org/about-us/newsroom/press-releases/researchers-compare-twoyear-clinical-outcomes-of-mitral-valve-replacement-and-repair-, Nov. 9, 2015, 2 pages.

Mueller et al., "An Overview of Mems-based Micropropulsion Developments at JPL", Acta Astronautica, vol. 52, No. 9-12, Selected Proceedings of the 3rd IAA International Symposium on Small Satellites for Earth Observation, May-Jun. 2003, 15 pages.

Mueller et al., "Design and Fabrication of MEMS-Based Micropropulsion Devices at JPL", Proceedings of SPIE vol. 4558, 2001, pp. 57-71.

(56) References Cited

OTHER PUBLICATIONS

Muller et al., "Remote Control Catheter Navigation: Options for Guidance Under MRI", Journal of Cardiovascular Magnetic Resonance, vol. 14, No. 33, Available online at http://www.jcmr-online.com/content/14/1/33, 2012, pp. 1-9.

Newmarker, "How Lasers are Changing MedTech", Lasers, Qmed, Available online at http://www.qmed.com/mpmn/medtechpulse/how-lasers-are-changing-medtechcid=nl.qmed02, Jan. 14, 2014, 3 pages.

Newmarker, "How Scotch Tape is Driving Diagnostics Breakthroughs", Medical Plastics, Qmed, Available online at http://www.qmed.com/mpmn/medtechpulse/how-scotch-tape-driving-diagnosticsbreakthroughscid=nl.qmed02.20141002, Oct. 1, 2014, 3 pages.

Nolker et al., "Differences in Tissue Injury and Ablation Outcomes in Atrial Fibrillation Patients—Manual versus Robotic Catheters", Journal of Atrial Fibrillation, Department of Cardiology, Heart and Diabetes Center, vol. 6, No. 2, Aug.-Sep. 2013, pp. 82-88.

Nucryovascular, LLC, "Peripheral Dilatation Catheter Peripheral Dilatation System", Vascular solutions, PolarCath™ over-the-wire, Available online at www.vasc.com, pp. 1-12.

Oh et al., "A Review of Microvalves", Topical Review, Journal of Micromechanics and Microengineering, vol. 16, 2006, pp. R13-R39.

Omed Qualified Suppliers, "A Tiny Spectrometer that Costs 10 Bucks", Qmed, Available online at http://www.qmed.com/mpmn/medtechpulse/tiny-spectrometer-costs-10-buckscid=nl.qmed02.20141216, Dec. 12, 2014, 3 pages.

Omed Qualified Suppliers, "How 3-D Printing Can Help Accelerate Fluidic Manifold Delivery", Qmed, Available online at http://www.qmed.com/mpmn/medtechpulse/how-3-d-printing-can-help-accelerate-fluidic-manifold-deliverycid=nl.qmed02.20150507, May 6, 2015, 3 pages.

Omed Qualified Suppliers, "Introducing 3-D Injection Molding", Qmed, Available online at http://www.qmed.com/mpmn/gallery/image/4-introducing-3-d-injection-molding, 2014, 2 pages.

Omed Qualified Suppliers, "Overcoming Engineering Challenges: Developing a Tiny Robotically Steerable Guidewire", Qmed, Medtech Pulse Blog, Available online at http://www.qmed.com/mpmn/medtechpulse/overcoming-engineering-challenges-developing-tiny-robotically-steerable-guidewirecid=nl_qmed_daily, Feb. 15, 2013, 2 pages.

Ono et al., "Development of a Cylinder Type Gas-liquid Phase-change Actuator", 2 pages.

Parmar, "FDA Approves St. Jude Medical's Force-Sensing Ablation Catheters for AF", Regulatory and Compliance, MDDI Medical Device and Diagnostic Industry, Available online at http://www.mddionline.com/article/fda-approves-st-jude-medicals-force-sensing-ablation-catheters-af-102714cid=nl.mddi01.20141028, Oct. 27, 2014, 3 pages.

Peelsil™ Tubing, "Scientific Tubing", SGE, Glass Lined Tubing (GLT™), Available online at www.sge.com, Fused Silica Tubing brochure PD-0230-Aw, 2001, 6 pages.

Penning et al., "A Combined Modal-Joint Space Control Approach for Minimally Invasive Surgical Continuum Manipulators", Advanced Robotics, vol. 28, No. 16, Jul. 2014, 41 pages.

Penning et al., "An Evaluation of Closed-Loop Control Options for Continuum Manipulators", IEEE, 2012, 6 pages.

Penning, "ICRA 2012 Recap", Available online at http://robotics.engr.wisc.edu/cgi-bin/wikiwp/2012/11/icra-2012-recap/, Nov. 11, 2012, 2 pages.

Penning et al., "Towards Closed Loop Control of a Continuum Robotic Manipulator for Medical Applications", IEEE, 2011, 6 pages.

Plastics, "Corrugator Technologies: Overview and New Developments", Corrugator technologies overview, Available at http://www.plastics.gl/extrusion-profile/corrugator-technologies-overview/, 2015, 8 pages.

Pollock, "Bionic Ants Could be Tomorrow's Factory Workers". Available online at http://www.reuters.com/article/2015/03/30/us-germany-bionic-ants-idUSKBN0MQ1WD20150330, Mar. 30, 2015, 3 pages.

Preston-Maher et al., "A Technical Review of Minimally Invasive Mitral Valve Replacements", Cardiovascular Engineering and Technology, vol. 6, No. 2, Jun. 2015, pp. 174-184.

Profilepipe Machinery Inc., "Convoluted Tubing to an Outer Diameter of 65 mm", Available online at http://www.profilepipe.com/small_corrugators.html, 2015, 2 pages.

Qmed Qualified Suppliers, "Tiny Artificial Muscles", Available online at http://www.qmed.com/mpmn/gallery/image/1-tiny-artificial-muscles, Jul. 14, 2016, 1 page.

Qmed, Electronic Components, "How Micro-Location Could Boost Healthcare IoT", Available online at http://www.qmed.com/mpmn/medtechpulse/how-micro-location-could-boost-healthcare-iotcid=nl.x.qmed02.edt.aud.qmed.20160606, Jun. 3, 2016, 2 pages.

Quero et al., "A Novel Pressure Balanced Microfluidic Valve", Proc. ISCAS, IEEE, 2002, pp. 1-4.

Rich et al., "Costs for Mitral Valve Surgery According to STS Preoperative Risk: Implications for Transcatheter Mitral Therapies", American Association for Thoracic Surgery, Available Online at http://aats.org/mitral/abstracts/2015/P165.cgi, 2016, 2 pages.

Roriz et al., "Fiber Optic Intensity-Modulated Sensors: A Review in Biomechanics", Photonic Sensors, vol. 2, No. 4, 2012, pp. 315-330.

Rossiter et al., "Printing 3D Dielectric Elastomer Actuators for Soft Robotics", SPIE Proceedings, vol. 7287, Apr. 6, 2009, 2 pages.

Schut, "Corrugator Vacuum Forming", Plastics Technology, Available online at http://www.ptonline.com/articles/'corrugator-vacuum-forming', Jul. 2005, 4 pages.

SGE Analytical Science, "Tubing, Stainless Steel Tubing and Terry-Tool Tubing Cutter", 2011, 10 pages.

Shoa et al., "Conducting Polymer Based Active Catheter for Minimally Invasive Interventions inside Arteries", Conf Proc IEEE Eng Med Biol Soc, Available online at http://mm.ece.ubc.ca/mediawiki/images/b/b7/PID616280.pdf, 2008, pp. 2063-2066.

Sparkfun, "Accelerometer, Gyro and IMU Buying Guide", Available online at https://www.sparkfun.com/pages/accel_gyro_guide, accessed from the internet on Jul. 14, 2016, 10 pages.

Strickland, "Inside an MRI, a Non-Metallic Robot Performs Prostate Surgery", Available online at http://spectrum.ieee.org/automaton/robotics/medical-robots/inside-an-mri-a-nonmetallic-robot-performs-prostate-surgery, Jul. 8, 2015, 3 pages.

Takizawa et al., "Development of a Microfine Active Bending Catheter Equipped with MIF Tactile Sensors", Available online at http://www.ics.forth.gr/bioloch/internal/papers/Olympus.pdf, 1999, 7 pages.

Taramasso et al., "Current Challenges in Interventional Mitral Valve Treatment", J. Thorac. Dis., vol. 7, No. 9, Available online at http://www.ncbi.nlm.nih.gov/pmc/articles/PMC4598533/, 2015, pp. 1536-1542.

Teleflex Incorporated, "Balloons and Balloon Catheters", Available online at http://www.teleflexmedicaloem.com/diagnostic-and-interventional-catheters/balloon-catheters/, 2015, 3 pages.

Temiz et al., "Lab-on-a-Chip Devices: How to Close and Plug the Lab", Microelectronic Engineering, vol. 132, 2015, pp. 156-175.

Tokai Medical Products Inc., "PTA Sphere-Curve", Available online at http://www.tokaimedpro.co.jp/en/products/2009/000056.html, Jul. 14, 2016, 2 pages.

Tung et al., "Laser-Machined Shape Memory Alloy Actuators for Active Catheters", Mechatronics, IEEE/ASME Transactions on, vol. 12, No. 4, Aug. 2007, pp. 439-446.

Van Oosten et al., "Printed Artificial Cilia from Liquid-crystal Network Actuators Modularly Driven by Light", Nature Materials, vol. 8, Available online at http://www.nature.com/nmat/journal/v8/n8/full/nmat2487.html, 2009, pp. 677-682.

Veeramani, "A Transformative Tool for Minimally Invasive Procedures: Design, Modeling and Real-time Control of a Polycrystalline Shape Memory Alloy Actuated Robotic Catheter", 2009, 198 pages.

Walters, "Gas-Flow Calculations: Don't Choke", Applied Flow Technology, Chemical Engineering, Available online at http://www.aft.com/documents/AFT-CE-Gasflow-Reprint.pdf, Jan. 2000, 8 pages.

Wasserman, "Edwards and Medtronic Turn up TAVR Competition with Positive Study Data", Available online at http://www.fiercemedicaldevices.com/story/edwards-and-medtronic-turn-tavr-competition-positive-study-data/2015-03-16, Mar. 16, 2015, 3 pages.

(56) References Cited

OTHER PUBLICATIONS

Webb et al., "Transcatheter Aortic Valve Implantation: The Evolution of Prostheses, Delivery Systems and Approaches", Archives of Cardiovascular Disease, vol. 105, 2012, pp. 153-159.
Weber et al., "Side-Selective Atrial Transseptal Laser Puncture", The Journal of Innovations in Cardiac Rhythm Management, vol. 4, Avaiable online at http://www.innovationsincrm.com/cardiac-rhythm-management/2013/december/524-side-selective-atrial-transseptal-laser-puncture, Dec. 2013, pp. 1481-1485.
Wirtl et al., "White Paper Piezo Technology in Pneumatic Valves", Festo AG & Co. KG, 2014, pp. 1-9.
Wood, "Early Results for Transcatheter Mitral Valve Replacement Reveal Complications and Challenges for the Long Road Ahead", Available online at http://www.tctmd.com/show.aspxid=133937, Feb. 22, 2016, 1 pages.
Wutzler et al., "Robotic Ablation of Atrial Fibrillation", Department of Cardiology, . Vis. Exp. (99), e52560, Available online at http://www.jove.com/video/52560/robotic-ablation-of-atrial-fibrillation, 2015, 14 pages.
Yang et al., "Leak-Tight Piezoelectric Microvalve for High-Pressure Gas Micropropulsion", Journal of Microelectromechanical Systems, vol. 13, No. 5, IEEE, Available Online at http://web.stevens.edu/ses/documents/fileadmin/documents/pdf/JMEMS_hp_valve.pdf, Oct. 2004, pp. 799-807.
Yarbasi et al., "On the Design of a Continuum Robot with Extendable Balloons", Department of Mechanical Engineering, 2015, 1 page.
You et al., "A Doubly Cross-Linked Nano-Adhesive for the Reliable Sealing of Flexible Microfluidic Devices", Lab Chip., vol. 13, No. 7, Available online at http://www.ncbi.nlm.nih.gov/pubmed/23381132, Apr. 2013, pp. 1266-1272.

\* cited by examiner

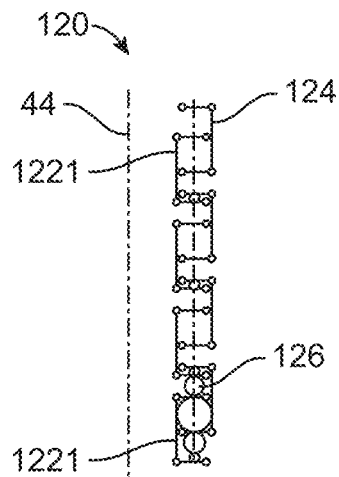
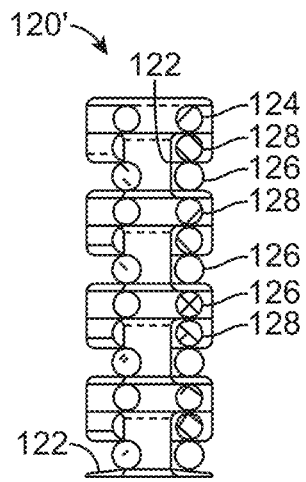
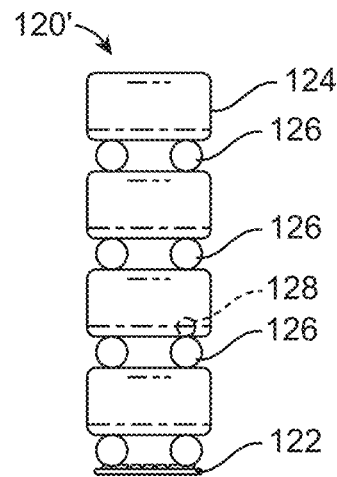
FIG. 13A  FIG. 13B  FIG. 13C
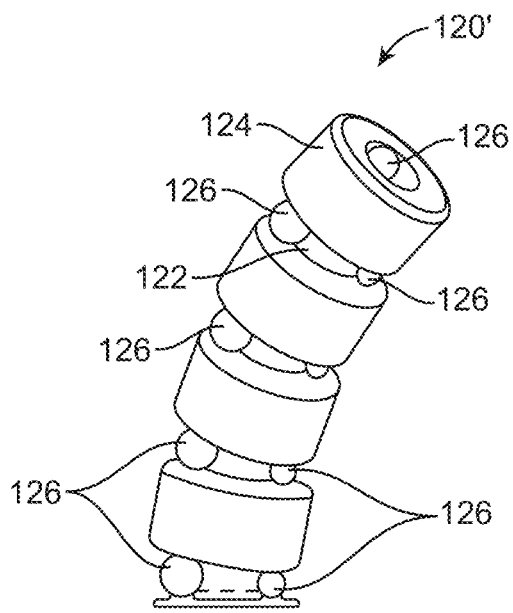
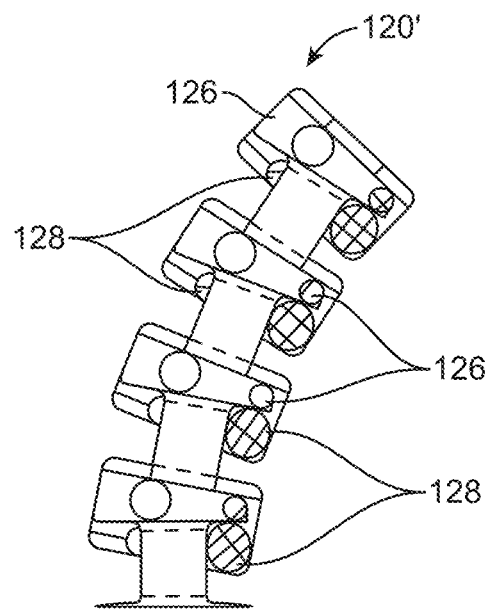
FIG. 13D  FIG. 13E

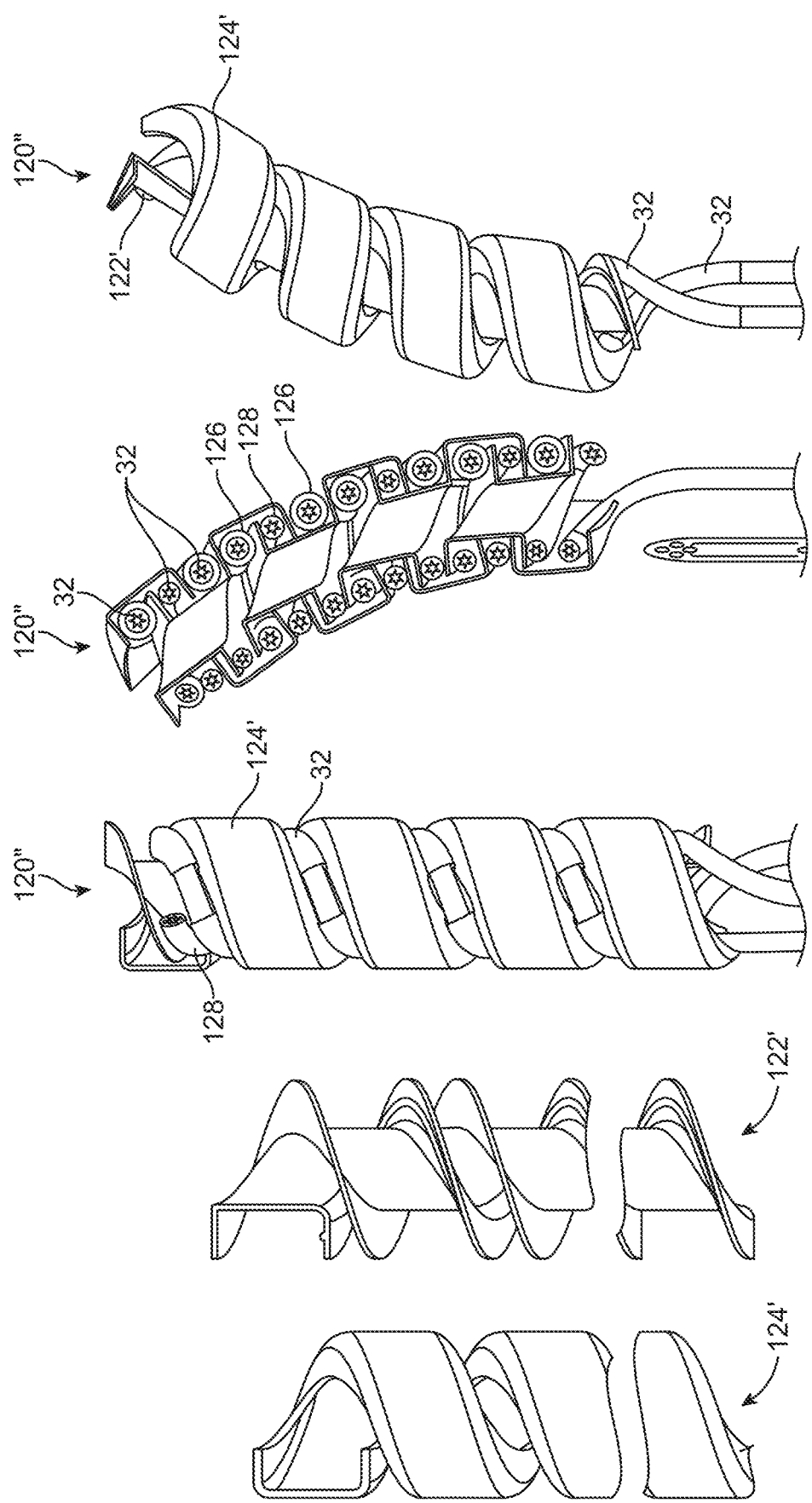

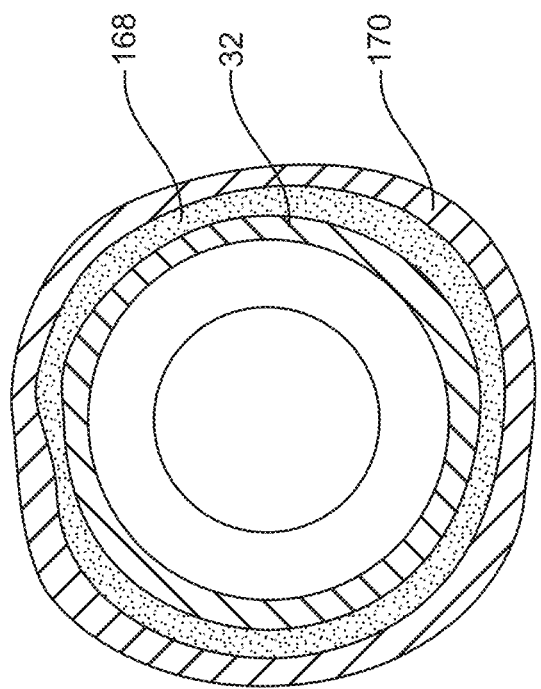
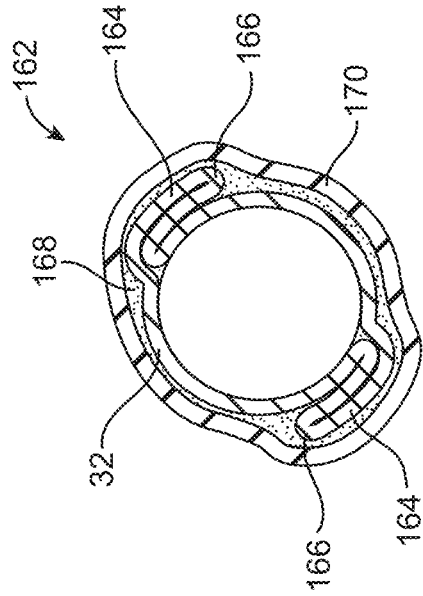
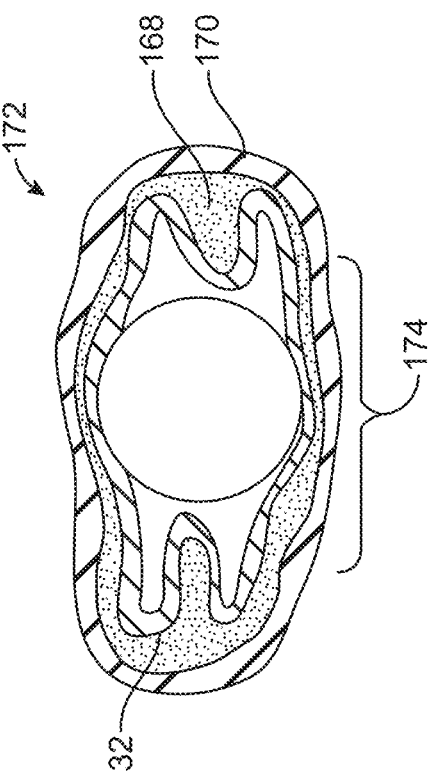

MATRIX SUPPORTED BALLOON ARTICULATION SYSTEMS, DEVICES, AND METHODS FOR CATHETERS AND OTHER USES

CROSS REFERENCE TO RELATED APPLICATIONS

The present application claims the benefit of U.S. Provisional Application Ser. No. 62/489,864, filed on Apr. 25, 2017, which is incorporated by reference herein in its entirety for all purposes.

FIELD OF THE INVENTION

In general, the present invention provides structures, systems, and methods for selectively bending or otherwise altering the bend characteristics of catheters and other elongate flexible bodies, the lengths of such bodies, and the like. In exemplary embodiments the invention provides articulated medical systems having a fluid-driven balloon array that can help shape, steer and/or advance a catheter, guidewire, or other elongate flexible structure along a body lumen. Alternative embodiments make use of balloon arrays for articulating (or altering the stiffness of) flexible manipulators and/or end effectors, industrial robots, borescopes, prosthetic fingers, robotic arms, positioning supports or legs, consumer products, or the like.

BACKGROUND OF THE INVENTION

Diagnosing and treating disease often involve accessing internal tissues of the human body, and open surgery is often the most straightforward approach for gaining access to internal tissues. Although open surgical techniques have been highly successful, they can impose significant trauma to collateral tissues.

To help avoid the trauma associated with open surgery, a number of minimally invasive surgical access and treatment technologies have been developed, including elongate flexible catheter structures that can be advanced along the network of blood vessel lumens extending throughout the body. While generally limiting trauma to the patient, catheter-based endoluminal therapies can be very challenging. A number of additional minimally invasive surgical technologies have also been developed, including robotic surgery, and robotic systems for manipulation of flexible catheter bodies from outside the patient have also previously been proposed. Some of those prior robotic catheter systems have met with challenges, in-part because of the difficulties in accurately controlling catheters using pull-wires. While the potential improvements to surgical accuracy make these efforts alluring, the capital equipment costs and overall burden to the healthcare system of these large, specialized systems is a concern.

A new technology for controlling the shape of catheters has recently been proposed which may present significant advantages over pull-wires and other known catheter articulation systems. As more fully explained in US Patent Publication No. US20160279388, entitled "Articulation Systems, Devices, and Methods for Catheters and Other Uses," published on Sep. 29, 2016 (assigned to the assignee of the subject application and the full disclosure of which is incorporated herein by reference), an articulation balloon array can include subsets of balloons that can be inflated to selectively bend, elongate, or stiffen segments of a catheter. These articulation systems can use pressure from a simple fluid source (such as a pre-pressurized canister) that remains outside a patient to change the shape of a distal portion of a catheter inside the patient via a series of channels in a simple multi-lumen extrusion, providing catheter control beyond what was previously available often without having to resort to a complex robotic gantry, without pull-wires, and even without motors. Hence, these new fluid-driven catheter systems appear to provide significant advantages.

Despite the advantages of the newly proposed fluid-driven catheter system, as with all successes, still further improvements would be desirable. In general, it would be beneficial to provide further improved articulation systems and devices, methods of articulation, and methods for making articulation structures. More specifically, it would be beneficial to identify assemblies and fabrication techniques that would facilitate the widespread use of articulation balloon arrays for altering the bending characteristics of catheters and other elongate flexible bodies. It would be particularly beneficial if these new technologies could simplify the overall structures, maintain alignment within balloon-array articulated structures during use, and/or reduce the costs for making and using these new articulated devices.

BRIEF SUMMARY OF THE INVENTION

The present invention generally provides improved articulation devices, systems, methods for articulation, along with methods for fabricating articulation structures. The articulations structures described herein will often include simple balloon arrays, with inflation of the balloons locally altering articulation. Liquid or gas inflation fluid may be directed toward the balloons from an inflation fluid source via a series of small channels in a simple extrusion, with the balloons and extrusions often being formed into a helical multi-balloon assembly. Advantageously, the balloons may be supported by encasing the helical balloon assembly in a polymer matrix, such as by winding the balloon assembly onto a mandrel and dip-coating some or all of the assembly in an elastomer such as a silicone, a urethane, or the like. The balloons may be supported by one or more spring, with loops of the spring(s) optionally being radially inward of the balloons, outward of the balloons, or interspersed between balloons (such as by using a flat wire spring having a cross section with a greater radial width than its axial height). In some embodiments, a mesh tube, braid, or other compliant materials may be included instead of or in addition to the spring. Relatively soft matrix materials (such as those having a durometer hardness of less than 30D) may help maintain alignment of the articulation system, and/or a highly elastic matrix (such as those capable of over 500% elongation and having a Shore A durometer hardness of 20 or more) can be used, optionally to help resiliently counteract pressure inside a partially inflated balloon, facilitate balloon deflation, and the like. Articulation balloon arrays may be disposed in an annular space bordered by inner and outer tubular sheaths, with a portion of one or both sheaths being axially slidable relative to the balloons so as to facilitate elongation and bending.

In a first aspect, the invention provides an elongate articulatable body comprising a first balloon string. The balloon string includes an inflation tube and a first set of balloons distributed along the inflation tube. The inflation tube has a first end and a second end with a first lumen extending therebetween. The balloons of the first set are in communication with the first lumen, and the first balloon string comprises a helical balloon coil having a helical axis. The balloons of the first set are offset from the helical axis along a first lateral bending axis. A first polymer matrix is disposed on the balloon string so as to help maintain alignment between the balloons of the first set when inflation fluid is transmitted through the first lumen and the balloons bend the helical axis laterally.

A number of optional general features are described herein that can be included, alone or in combinations, in the devices, systems, and methods. Optionally, the inflation tube(s) are integral with the balloons, with the balloons being formed by locally increasing a diameter of the inflation tube so that a relatively small profile segment of the inflation tube extends between adjacent balloons. A multi-lumen shaft may be included in the balloon string to facilitate inflation of selected subsets of the balloons, and/or multiple balloon strings (typically comprising 2, 3, or 4 strings along at least a portion of the articulatable body, but optionally more) may be included. For example, a second balloon string may be interleaved with the first in a double helix arrangement, with the first set of balloons on the first balloon string being aligned for articulation toward one lateral bending axis, and the second balloon string having a second set of balloons aligned for articulation toward another lateral bending axis; a third balloon string may optionally also be interleaved to provide bending in a third bending axis, and so on. Regardless, the first matrix optionally comprises an elastomeric polymer coating over the first balloon string, with some portion (or all) of first set of balloons and/or the inflation tube being embedded in the first matrix. Such embedding of the balloons and/or inflation tube in the matrix may optionally be performed so that some or all of the balloons, some or all of the inflation tube segments between balloons, or both, are fully encapsulated or encased in the first polymer matrix. Elastomeric matrices that are sufficiently soft to conform and accommodate balloon inflation and associated articulation of the elongate body may be used, with some matrices locally separating from the materials of the balloons, and/or accommodating local matrix fractures while maintaining balloon alignment. Exemplary first matrix materials comprise one or more of a first silicone, latex, polyisoprene, urethane, polyurethane, a thermoplastic, a thermoplastic elastomer, polyether block amide (PEBA) such as a PEBAX™ polymer or a Vestamid™ polymer, and/or a nitrile. The first matrix will often have a Shore durometer hardness of less than 20 A, optionally being 10 A or less, and in many cases being 5 A or less.

Typically, the balloon coil defines a plurality of circumferential loops, and each balloon of the first set will often be disposed on an associated loop. The first matrix is optionally contiguous between some or all of the adjacent loops. Alternatively, at least one additional helical body may be disposed between adjacent loops of the balloon coil. The additional helical body may have a plurality of other loops, and the first matrix can couple the loops of the balloon coil to adjacent loops of the at least one additional helical body. For example, the first spring can comprise a flat spring disposed axially between loops of the balloon coil.

In some embodiments, an additional body may be included, with the additional body comprising a first spring supporting the balloon coil so as to bias the axis toward a straight configuration and/or to urge the balloons from a fully inflated state toward an at least partially deflated state. The matrix can help to couple the first spring to the coil. The first spring can be disposed radially inward of the balloon coil or radial outward of the balloon coil. In fact, the balloon coil can optionally be disposed radially between the first spring and a second spring. The springs may comprise round wire structures, or at least the first spring may comprise a spring member with a flat cross-section having an axial thickness and a radial width greater than the axial thickness, such as a machined spring (optionally being laser cut from a tube), a 3D printed spring, a wound flat wire, or the like. The first spring optionally has a plurality of spring members, such as a multiple start machine spring or the like, particularly where multiple balloon strings are arranged in a double helix, a triple helix, or other multi-helix segments.

To provide a desired combination of articulation and stiffness characteristics, a second polymer matrix may be disposed over the first matrix. The second matrix will often comprise an elastomeric coating encompassing at least one of the first spring and/or the second spring. The second matrix may comprise a material that is adhereable to, compatible with, structurally similar to (but having a different hardness or other characteristic), or even the same as a material of the first matrix. Typically, the second matrix will be adhered to the first matrix. In many embodiments, the second matrix will have a Shore hardness durometer greater than that of the first matrix, and/or may have an elongation and breaking strength that is higher than that of the first matrix. Optionally, the balloon strings of the articulatable segments described herein may be wound with a first orientation, and one or two springs may be radially offset from the balloon string (with the balloon string often being racially captured between the two. The spring or springs may be wound with a second orientation opposed to the first orientation so that loops of the spring(s) cross loops of the balloon string. This can help the loops of the spring radially restrain radial expansion of the balloon so as to enhance axial elongation of the balloon during inflation, and may thus increase lateral bending articulation. Counter-winding these structures may also help limit unwinding (and associated non-planar articulation) when a subset of balloons along one side of the segment is inflated.

In another aspect, the invention provides a method for fabricating an articulating catheter. The method comprises fabricating a balloon string including: a) an inflation member having a first end and a second end with at a first lumen extending therebetween; and b) a first set of balloons distributed along the inflation member. The balloons of the first set can be in communication with the first lumen. The balloon string is formed into a helical coil (the coil having a helical axis with the balloons of the first set being laterally offset from the helical axis along a first lateral bending axis). The helical coil is embedded in a first polymer matrix such that the matrix helps maintain alignment between the balloons of the first set when inflation fluid is transmitted through the first lumen (optionally such that the inflating balloons laterally bend the helical axis laterally toward the first bending axis).

In another aspect, the invention provides an elongate articulatable body comprising an articulation balloon array having a proximal end, a distal end, and an axis therebetween. The articulation balloon array defines a tubular cross-section having an outer array profile and an inner array profile. An outer sheath has an axial outer sheath lumen, the outer sheath lumen receiving the articulation balloon array therein so that a surface of the outer sheath is adjacent the outer array profile. An inner sheath has an axial lumen, the inner sheath disposed within the articulation balloon array so that a surface of the inner sheath is adjacent the inner array profile. One of the sheaths (and preferably both of the sheaths) have a first portion axially affixed to one of the ends of the articulation balloon array and a second portion axially movable relative to the articulation balloon array so as to facilitate articulation of the articulatable body by the articulation balloon array.

A number of preferred features can be provided, either individually or in combinations. For example, the articulation balloon array may comprise a helical balloon array distributed along a plurality of helical loops. A helical frame can be disposed between the loops of the balloon array, and the inner and outer sheaths may be radially sealed so as to inhibit radial transmission of any inflation fluid leaking from the balloon array. The inner and outer sheath can be sealed together adjacent the distal end of the articulation balloon array so that any inflation fluid that is contained in an annular balloon array space is directed proximally out of the patient. The surfaces of the inner and outer sheath adjacent the proximal end of the articulation balloon array can be relatively smooth, low friction, and optionally lubricious surfaces so that they can slide axially along the articulation balloon array and the adjacent helical frame proximally of the affixed and sealed distal end. This sliding relative motion between these adjacent components can facilitate axial elongation of the articulable body and/or lateral bending of the articulatable body, for example, under bending or elongation forces imposed by inflation of some or all of the balloons of the articulation balloon array.

Additional or alternative refinements may also be included. For example, the helical frame preferably comprises a flat-wire helical spring having axially opposed major surfaces. The frame can be formed with a first wound orientation (such as being a right-hand spring). The inner sheath optionally comprises a first elastomeric polymer layer having a first surface, with the elastomeric polymer comprising any of the elastomeric polymers described herein. An inner reinforcing coil can be disposed radially inward of the first surface, the inner reinforcing coil having a second wound orientation opposed to the first wound orientation. This can help orient multiple winds of the coil across most or all of the individual articulation balloons, making it easier for the coil to radially constrain the balloon within the frame and inhibiting deleterious radial migration of the balloons out from the desired location between the major surfaces of adjacent loops of the flat spring. Optionally, the outer sheath may include a second elastomeric polymer layer having a second surface and an outer reinforcing coil disposed radially outward of the second surface, the outer reinforcing coil having the second wound orientation.

BRIEF DESCRIPTION OF THE DRAWINGS

FIGS. 13A-13E schematically illustrate frame systems having axially opposed elongation and contraction balloons for locally elongating and bending a catheter or other elongate flexible body.

FIGS. 14A-14E schematically illustrate frame systems having axially opposed elongation and contraction balloons similar to those of FIGS. 13A-13E, with the frames comprising helical structures.

FIGS. 16A-16C schematically illustrate cross-sections of balloons dip-coated in a low-strength polymer matrix while deflated and folded, and then at least partially embedded in an elastically distensible dip-coat polymer matrix so as to allow expansion and subsequent controlled deflation to a small-profile configuration.

DETAILED DESCRIPTION OF THE INVENTION

Figure 1:
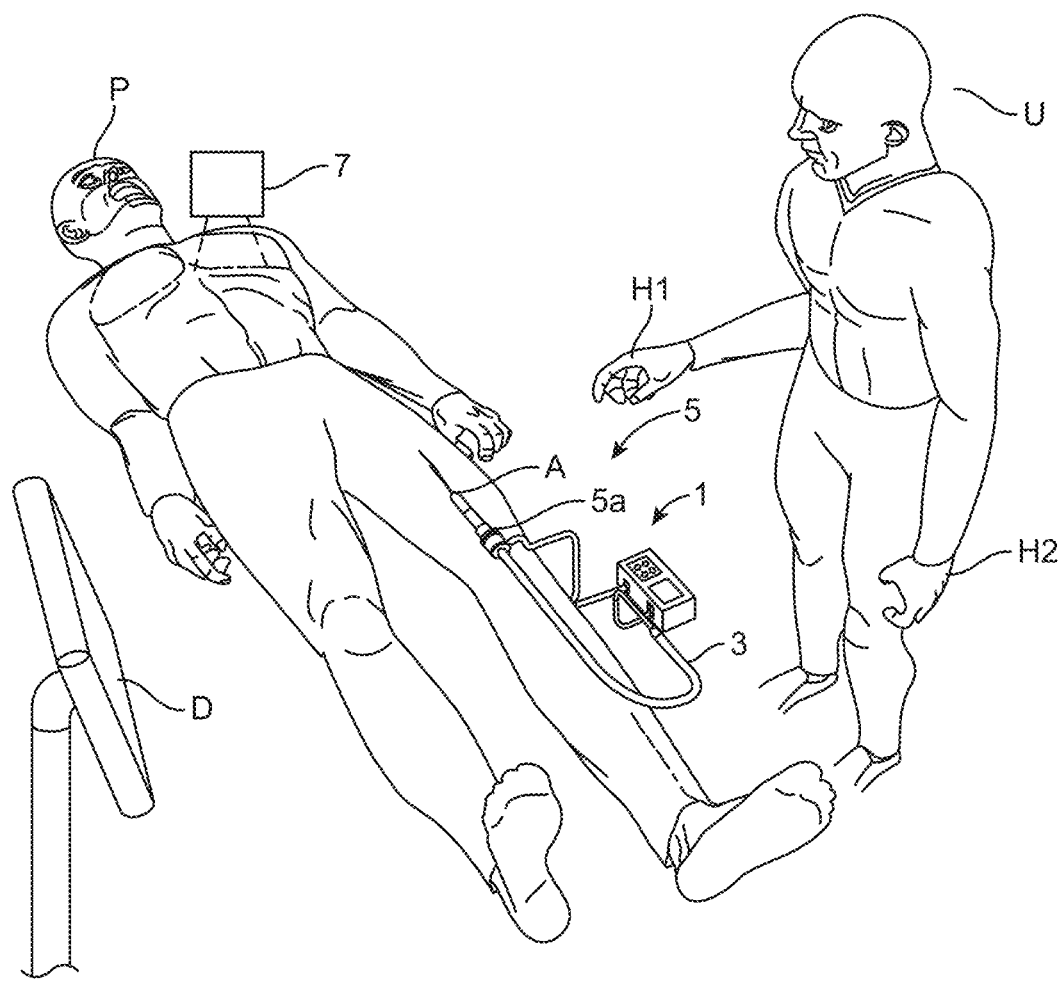
FIG. 1 is a simplified perspective view of a medical procedure in which a physician can input commands into a catheter system so that a catheter is articulated using systems and devices described herein.

The present invention generally provides fluid control devices, systems, and methods that are particularly useful for articulating catheters and other elongate flexible structures. The structures described herein will often find applications for diagnosing or treating the disease states of or adjacent to the cardiovascular system, the alimentary tract, the airways, the urogenital system, and/or other lumen systems of a patient body. Other medical tools making use of the articulation systems described herein may be configured for endoscopic procedures, or even for open surgical procedures, such as for supporting, moving and aligning image capture devices, other sensor systems, or energy delivery tools, for tissue retraction or support, for therapeutic tissue remodeling tools, or the like. Alternative elongate flexible bodies that include the articulation technologies described herein may find applications in industrial applications (such as for electronic device assembly or test equipment, for orienting and positioning image acquisition devices, or the like). Still further elongate articulatable devices embodying the techniques described herein may be configured for use in consumer products, for retail applications, for entertainment, or the like, and wherever it is desirable to provide simple articulated assemblies with multiple degrees of freedom without having to resort to complex rigid linkages.

Embodiments provided herein may use balloon-like structures to effect articulation of the elongate catheter or other body. The term "articulation balloon" may be used to refer to a component which expands on inflation with a fluid and is arranged so that on expansion the primary effect is to cause articulation of the elongate body. Note that this use of such a structure is contrasted with a conventional interventional balloon whose primary effect on expansion is to cause substantial radially outward expansion from the outer profile of the overall device, for example to dilate or occlude or anchor in a vessel in which the device is located. Independently, articulated medial structures described herein will often have an articulated distal portion, and an unarticulated proximal portion, which may significantly simplify initial advancement of the structure into a patient using standard catheterization techniques.

The catheter bodies (and many of the other elongate flexible bodies that benefit from the inventions described herein) will often be described herein as having or defining an axis, such that the axis extends along the elongate length of the body. As the bodies are flexible, the local orientation of this axis may vary along the length of the body, and while the axis will often be a central axis defined at or near a center of a cross-section of the body, eccentric axes near an outer surface of the body might also be used. It should be understood, for example, that an elongate structure that extends "along an axis" may have its longest dimension extending in an orientation that has a significant axial component, but the length of that structure need not be precisely parallel to the axis. Similarly, an elongate structure that extends "primarily along the axis" and the like will generally have a length that extends along an orientation that has a greater axial component than components in other orientations orthogonal to the axis. Other orientations may be defined relative to the axis of the body, including orientations that are transvers to the axis (which will encompass orientation that generally extend across the axis, but need not be orthogonal to the axis), orientations that are lateral to the axis (which will encompass orientations that have a significant radial component relative to the axis), orientations that are circumferential relative to the axis (which will encompass orientations that extend around the axis), and the like. The orientations of surfaces may be described herein by reference to the normal of the surface extending away from the structure underlying the surface. As an example, in a simple, solid cylindrical body that has an axis that extends from a proximal end of the body to the distal end of the body, the distal-most end of the body may be described as being distally oriented, the proximal end may be described as being proximally oriented, and the surface between the proximal and distal ends may be described as being radially oriented. As another example, an elongate helical structure extending axially around the above cylindrical body, with the helical structure comprising a wire with a square cross section wrapped around the cylinder at a 20 degree helix angle, might be described herein as having two opposed axial surfaces (with one being primarily proximally oriented, one being primarily distally oriented). The outermost surface of that wire might be described as being oriented exactly radially outwardly, while the opposed inner surface of the wire might be described as being oriented radially inwardly, and so forth.

Referring first to FIG. 1, a first exemplary catheter system 1 and method for its use are shown. A physician or other system user U interacts with catheter system 1 so as to perform a therapeutic and/or diagnostic procedure on a patient P, with at least a portion of the procedure being performed by advancing a catheter 3 into a body lumen and aligning an end portion of the catheter with a target tissue of the patient. More specifically, a distal end of catheter 3 is inserted into the patient through an access site A, and is advanced through one of the lumen systems of the body (typically the vasculature network) while user U guides the catheter with reference to images of the catheter and the tissues of the body obtained by a remote imaging system.

Exemplary catheter system 1 will often be introduced into patient P through one of the major blood vessels of the leg, arm, neck, or the like. A variety of known vascular access techniques may also be used, or the system may alternatively be inserted through a body orifice or otherwise enter into any of a number of alternative body lumens. The imaging system will generally include an image capture system 7 for acquiring the remote image data and a display D for presenting images of the internal tissues and adjacent catheter system components. Suitable imaging modalities may include fluoroscopy, computed tomography, magnetic resonance imaging, ultrasonography, combinations of two or more of these, or others.

Catheter 3 may be used by user U in different modes during a single procedure. More specifically, at least a portion of the distal advancement of catheter 3 within the patient may be performed in a manual mode, with system user U manually manipulating the exposed proximal portion of the catheter relative to the patient using hands H1, H2. In addition to such a manual movement mode, catheter system 1 may also have a 3-D automated movement mode using computer controlled articulation of at least a portion of the length of catheter 3 disposed within the body of the patient to change the shape of the catheter portion, often to advance or position the distal end of the catheter. Movement of the distal end of the catheter within the body will often be provided per real-time or near real-time movement commands input by user U. Still further modes of operation of system 1 may also be implemented, including concurrent manual manipulation with automated articulation, for example, with user U manually advancing the proximal shaft through access site A while computer-controlled lateral deflections and/or changes in stiffness over a distal portion of the catheter help the distal end follow a desired path or reduce resistance to the axial movement. Additional details regarding modes of use of catheter 3 can be found in US Patent Publication No. US20160279388, entitled "Articulation Systems, Devices, and Methods for Catheters and Other Uses," published on Sep. 29, 2016, assigned to the assignee of the subject application, the full disclosure of which is incorporated herein by reference.

Figure 2A:
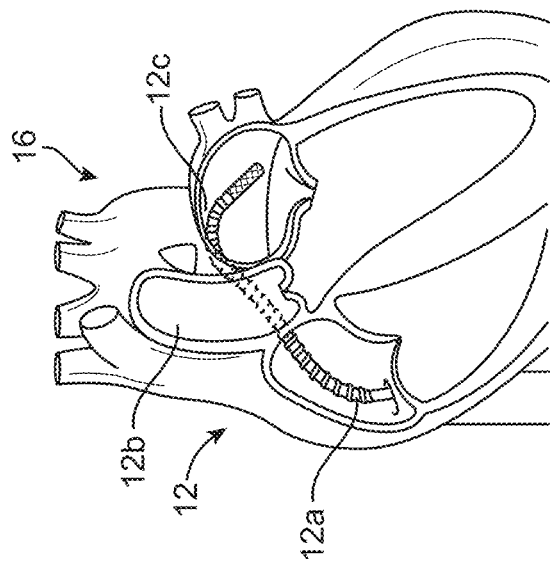
FIGS. 2A-2C schematically illustrates a catheter having a distal portion with an axial series of articulated segments supporting a prosthetic mitral valve, and show how the segments articulate so as to change the orientation and location of the valve.
Figure 2B:
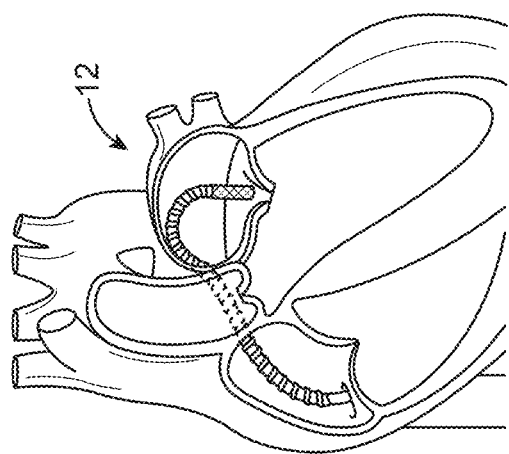
Figure 2C:
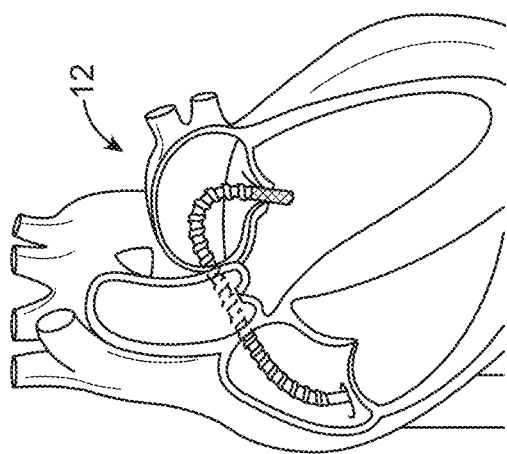
Figure 3A:
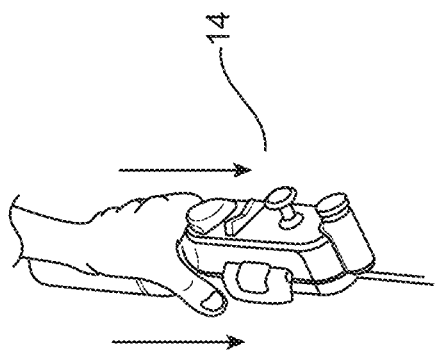
FIGS. 3A-3C schematically illustrate input command movements to change the orientation and location of the valve, with the input commands corresponding to the movements of the valve so as to provide intuitive catheter control.
Figure 3B:
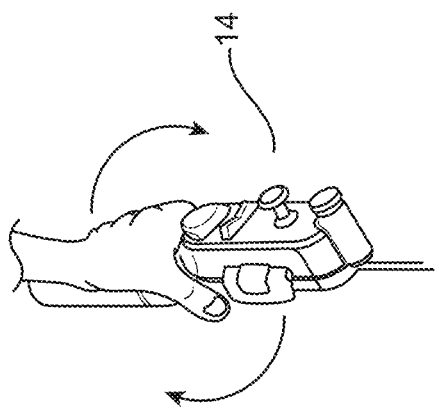
Figure 3C:
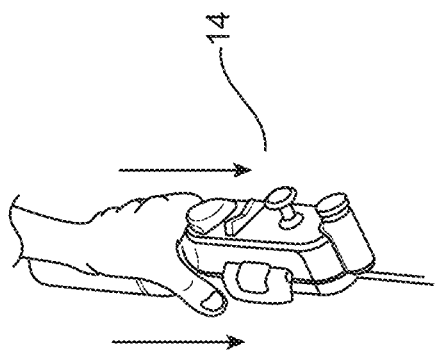

Referring now to FIGS. 2A-3C, devices and methods are shown for controlling movement of the distal end of a multi-segment articulated catheter 12 using a movement command input device 14 in a catheter system similar system 1 (described above). Multi-segment catheter 12 is shown in FIG. 2A extending within a heart 16, and more specifically with a distal portion of the catheter extending up to the heart via the inferior vena cava, with a first, proximal articulatable segment 12a bending within a right atrium of the heart toward a trans-septal access site. A second, intermediate articulatable segment 12b traverses the septum, and a third, distal articulatable segment 12c has some bend inside the left atrium of the heart 16. A tool, such as a prosthetic mitral valve, is supported by the distal segment 12c, and the tool is not in the desired position or orientation for use in the image of FIG. 2A. As shown in FIG. 3A, input device 14 is held by the hand of the user in an orientation that, very roughly, corresponds to the orientation of the tool (typically as the tool is displayed to the user in the display of the image capture system, as described above).

Referring to FIGS. 2A, 2B, 3A, and 3B, to change an orientation of the tool within the heart the user may change an orientation of input device 14, with the schematic illustration showing the input command movement comprising a movement of the housing of the overall input device. The change in orientation can be sensed by sensors supported by the input housing (with the sensors optionally comprising orientation or pose sensors similar to those of smart phones, tablets, game controllers, or the like). In response to this input, the proximal, intermediate, and distal segments 12A, 12B, and 12C of catheter 12 may all change shape so as to produce the commanded change in orientation of the tool. The changes in shapes of the segments will be calculated by a robotic processor of the catheter system, and the user may monitor the implementation of the commanded movement via the image system display. Similarly, as can be understood with reference to FIGS. 2B, 2C, 3B, and 3C, to change a position of the tool within the heart the user may translate input device 14. The commanded change in position can again be sensed and used to calculate changes in shape to the proximal, intermediate, and distal segments 12A, 12B, and 12C of catheter 12 so as to produce the commanded translation of the tool. Note that even a simple change in position or orientation (or both) will often result in changes to shape in multiple articulated segments of the catheter, particularly when the input movement command (and the resulting tool output movement) occur in three dimensional space within the patient.

Figure 4:
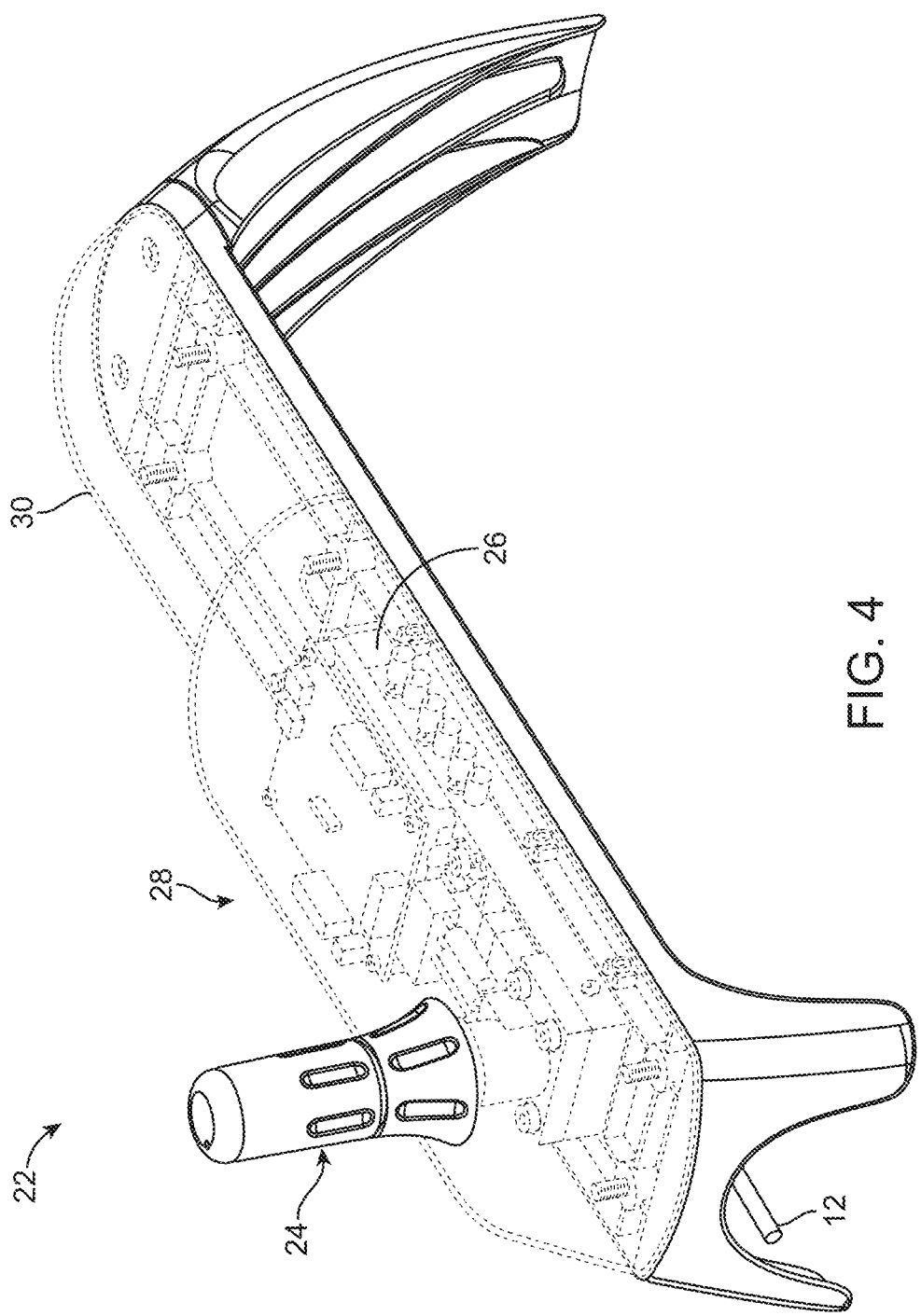
FIG. 4 is a partially see-through perspective view of an exemplary fluid drive manifold system for articulating a balloon array so as to control the shape of a valve delivery catheter or other elongate flexible body.

Referring to FIG. 4, an exemplary articulated catheter drive system 22 includes a pressurized fluid source 24 coupled to catheter 12 by a manifold 26. The fluid source preferably comprises a receptacle for and associated disposable canister containing a liquid/gas mixture, such as a commercially available nitrous oxide (N2O) canister. Manifold 26 may have a series of valves and pressure sensors, and may optionally include a reservoir of a biocompatible fluid such as saline that can be maintained at pressure by gas from the canister. The valves and reservoir pressure may be controlled by a processor 28, and a housing 30 of drive system 22 may support a user interface configured for inputting of movement commands for the distal portion of the catheter, as more fully explained in co-pending U.S. patent application Ser. No. 15/369,606, entitled "INPUT AND ARTICULATION SYSTEM FOR CATHETERS AND OTHER USES," filed on Dec. 5, 2016 (the full disclosure of which is incorporated herein by reference).

Regarding processor 28 and the other data processing components of drive system 22, it should be understood that a variety of data processing architectures may be employed. The processor, pressure or position sensors, and user interface will, taken together, typically include both data processing hardware and software, with the hardware including an input (such as a joystick or the like that is movable relative to housing 30 or some other input base in at least 2 dimensions), an output (such as a sound generator, indicator lights, and/or an image display, and one or more processor board. These components are included in a processor system capable of performing the rigid-body transformations, kinematic analysis, and matrix processing functionality associated with generating the valve commands, along with the appropriate connectors, conductors, wireless telemetry, and the like. The processing capabilities may be centralized in a single processor board, or may be distributed among the various components so that smaller volumes of higher-level data can be transmitted. The processor(s) will often include one or more memory or storage media, and the functionality used to perform the methods described herein will often include software or firmware embodied therein. The software will typically comprise machine-readable programming code or instructions embodied in non-volatile media, and may be arranged in a wide variety of alternative code architectures, varying from a single monolithic code running on a single processor to a large number of specialized subroutines being run in parallel on a number of separate processor sub-units.

Figure 5:
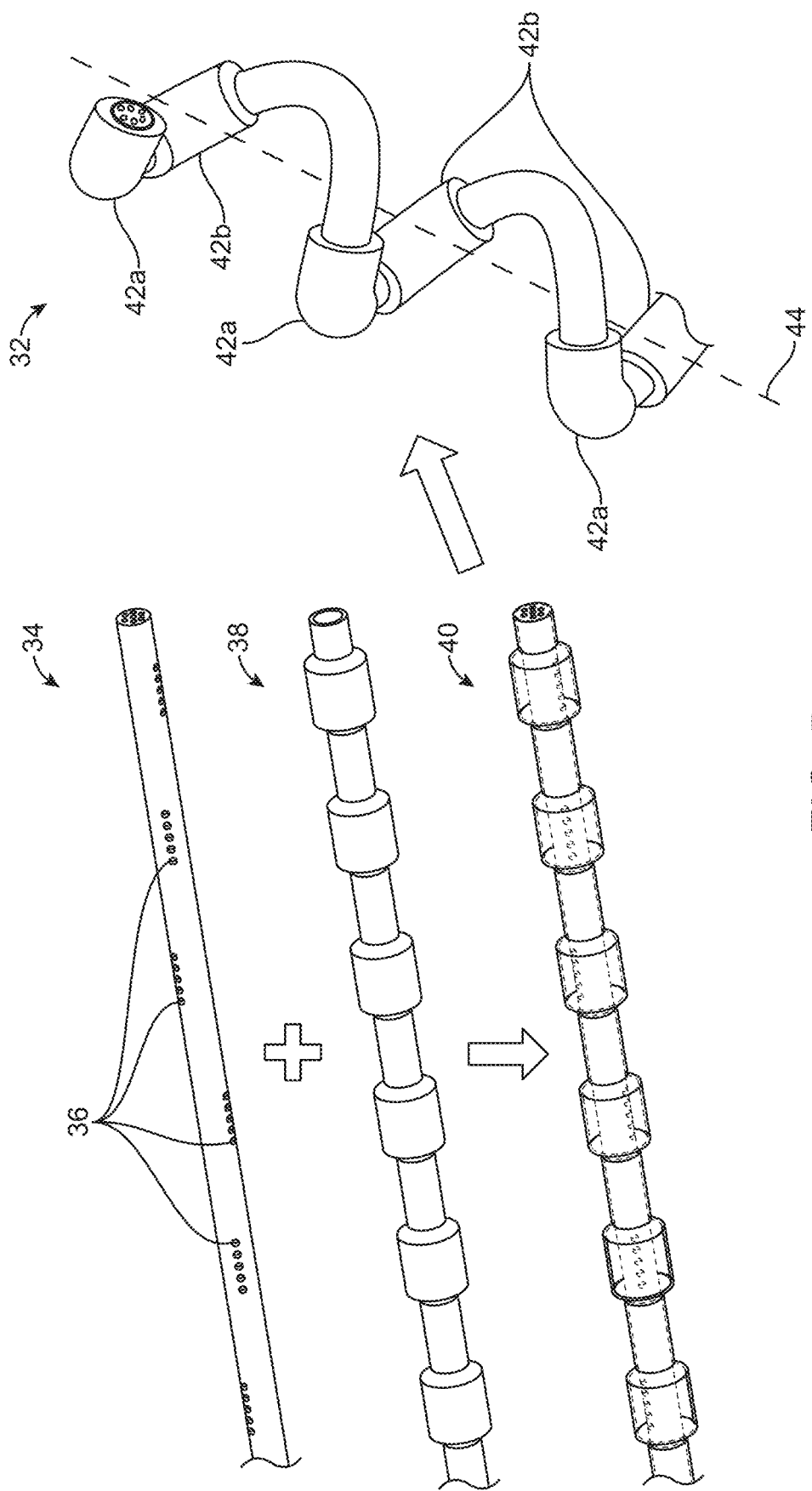
FIG. 5 is a simplified schematic illustration of components of a helical balloon assembly, showing how an extruded multi-lumen shaft can be assembled to provide fluid to laterally aligned subsets of the balloons.

Referring now to FIG. 5, the components of, and fabrication method for production of, an exemplary balloon array assembly, sometimes referred to herein as a balloon string 32, can be understood. A multi-lumen shaft 34 will typically have between 2 and 18 lumens. The shaft can be formed by extrusion with a polymer such as a nylon, a polyurethane, a thermoplastic such as a Pebax™ thermoplastic or a polyether ether ketone (PEEK) thermoplastic, a polyethylene terephthalate (PET) polymer, a polytetrafluoroethylene (PTFE) polymer, or the like. A series of ports 36 are formed between the outer surface of shaft 34 and the lumens, and a continuous balloon tube 38 is slid over the shaft and ports, with the ports being disposed in large profile regions of the tube and the tube being sealed over the shaft along the small profile regions of the tube between ports to form a series of balloons. The balloon tube may be formed using any compliant, non-compliant, or semi-compliant balloon material such as a latex, a silicone, a nylon elastomer, a polyurethane, a nylon, a thermoplastic such as a Pebax™ thermoplastic or a polyether ether ketone (PEEK) thermoplastic, a polyethylene terephthalate (PET) polymer, a polytetrafluoroethylene (PTFE) polymer, or the like, with the large-profile regions preferably being blown sequentially or simultaneously to provide desired hoop strength. The shaft balloon assembly 40 can be coiled to a helical balloon array of balloon string 32, with one subset of balloons 42a being aligned along one side of the helical axis 44, another subset of balloons 44b (typically offset from the first set by 120 degrees) aligned along another side, and a third set (shown schematically as deflated) along a third side. Alternative embodiments may have four subsets of balloons arranged in quadrature about axis 44, with 90 degrees between adjacent sets of balloons.

Figures 6A, 6B, 6C:
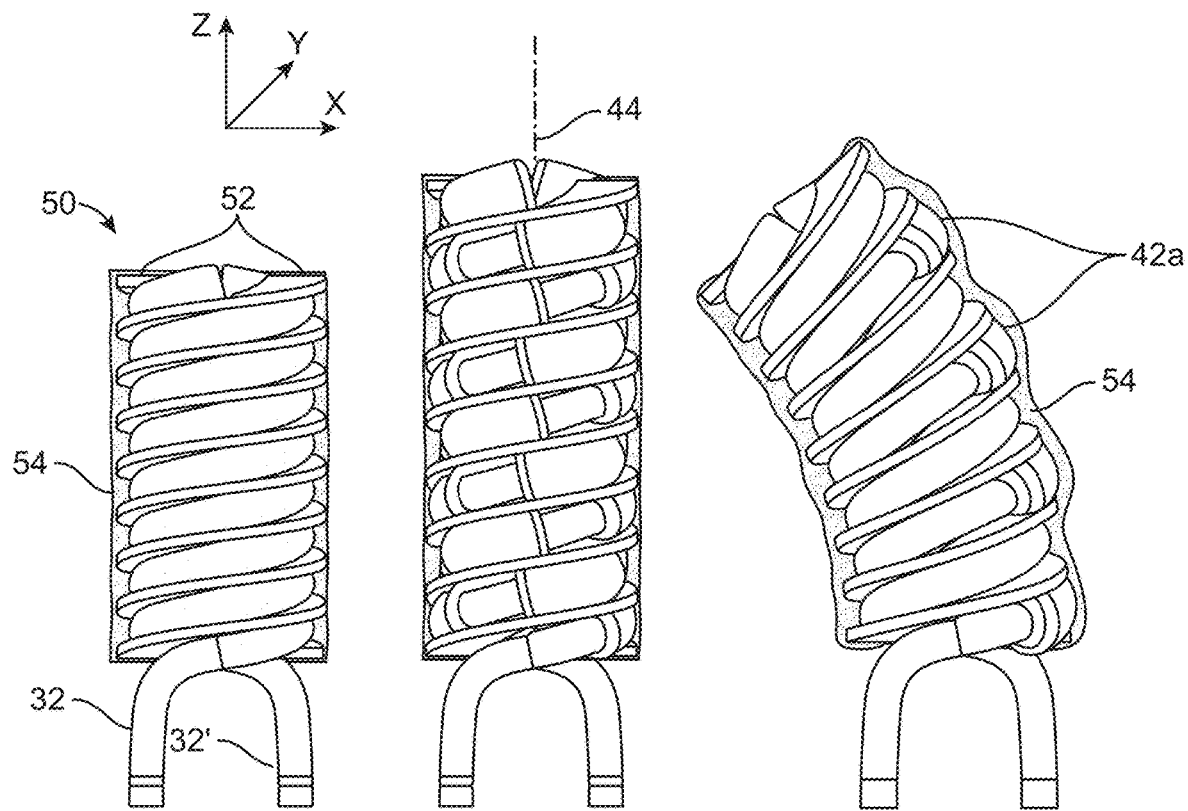
FIGS. 6A-6C schematically illustrate helical balloon assemblies supported by flat springs and embedded in an elastomeric polymer matrix, and show how selective inflation of subsets of the balloons can elongate and laterally articulate the assemblies.

Referring now to FIGS. 6A, 6B, and 6C, an articulated segment assembly 50 has a plurality of helical balloon strings 32, 32' arranged in a double helix configuration. A pair of flat springs 52 are interleaved between the balloon strings and can help axially compress the assembly and urge deflation of the balloons. As can be understood by a comparison of FIGS. 6A and 6B, inflation of subsets of the balloons surrounding the axis of segment 50 can induce axial elongation of the segment. As can be understood with reference to FIGS. 6A and 6C, selective inflation of a balloon subset 42a offset from the segment axis 44 along a common lateral bending orientation X induces lateral bending of the axis 44 away from the inflated balloons. Variable inflation of three or four subsets of balloons (via three or four channels of a single multi-lumen shaft, for example) can provide control over the articulation of segment 50 in three degrees of freedom, i.e., lateral bending in the +/−X orientation and the +/−Y orientation, and elongation in the +Z orientation. As noted above, each multilumen shaft of the balloon strings 32, 32' may have more than three channels (with the exemplary shafts having 6 lumens), so that the total balloon array may include a series of independently articulatable segments (each having 3 or 4 dedicated lumens of one of the multi-lumen shafts, for example).

Referring still to FIGS. 6A, 6B, and 6C, articulated segment 50 includes a polymer matrix 54, with some or all of the outer surface of balloon strings 32, 32' and flat springs 52 that are included in the segment being covered by the matrix. Matrix 54 may comprise, for example, a relatively soft elastomer to accommodate inflation of the balloons and associated articulation of the segment, with the matrix optionally helping to urge the balloons toward an at least nominally deflated state, and to urge the segment toward a straight, minimal length configuration. Advantageously, matrix 54 can maintain overall alignment of the balloon array and springs within the segment despite segment articulation and bending of the segment by environmental forces.

Segment 50 may be assembled by, for example, winding springs 52 together over a mandrel and restraining the springs with open channels between the axially opposed spring surfaces. Balloon strings 32, 32' can be wrapped over the mandrel in the open channels. The balloons may be fully inflated, partially inflated, nominally inflated (sufficiently inflated to promote engagement of the balloon wall against the opposed surfaces of the adjacent springs without driving the springs significantly wider apart than the diameter of the balloon string between balloons), deflated, or deflated with a vacuum applied to locally flatten and maintain 2 or 4 opposed outwardly protruding pleats or wings of the balloons. The balloons may be pre-folded, gently pre-formed at a moderate temperature to bias the balloons toward a desired fold pattern, or unfolded and constrained by adjacent components of the segment (such as the opposed surfaces of the springs and/or other adjacent structures) urge the balloons toward a consistent deflated shape. When in the desired configuration, the mandrel, balloon strings, and springs can then be dip-coated in a pre-cursor liquid material of polymer matrix 54, with repeated dip-coatings optionally being performed to embed the balloon strings and springs in the matrix material and provide a desired outer coating thickness. Alternatively, matrix 54 can be over-molded onto, sprayed or poured over, brushed onto or otherwise applied to the balloon strings and springs, with the balloons and other assembly components optionally being supported by a spinning mandrel, or the like. The liquid material can be evened by rotating the coated assembly, by passing the assembly through an aperture, by manually troweling matrix material over the assembly, or the like. Curing of the matrix may be provided by heating (optionally while rotating about the axis), by application of light, by inclusion of a cross-linking agent in the matrix, or the like. The polymer matrix may remain quite soft in some embodiments, optionally having a Shore A durometer hardness of 2-30, typically being 3-25, and optionally being almost gel-like. Other polymer matrix materials may be somewhat harder (and optionally being used in somewhat thinner layers), having Shore A hardness durometers in a range from about 20 to 95, optionally being from about 30 to about 60. Suitable matrix materials comprise elastomeric urethane polymers, polyurethane polymers, silicone polymers, latex polymers, polyisoprene polymers, nitrile polymers, plastisol polymers, thermoplastic elastomers, polyether block amide polymers (such as PEBAX™ polymers or Vestamid™ polymers), or the like. Regardless, once the polymer matrix is in the desired configuration, the balloon strings, springs, and matrix can be removed from the mandrel. Optionally, flexible inner and/or outer sheath layers may be added.

Figures 7A, 7B:
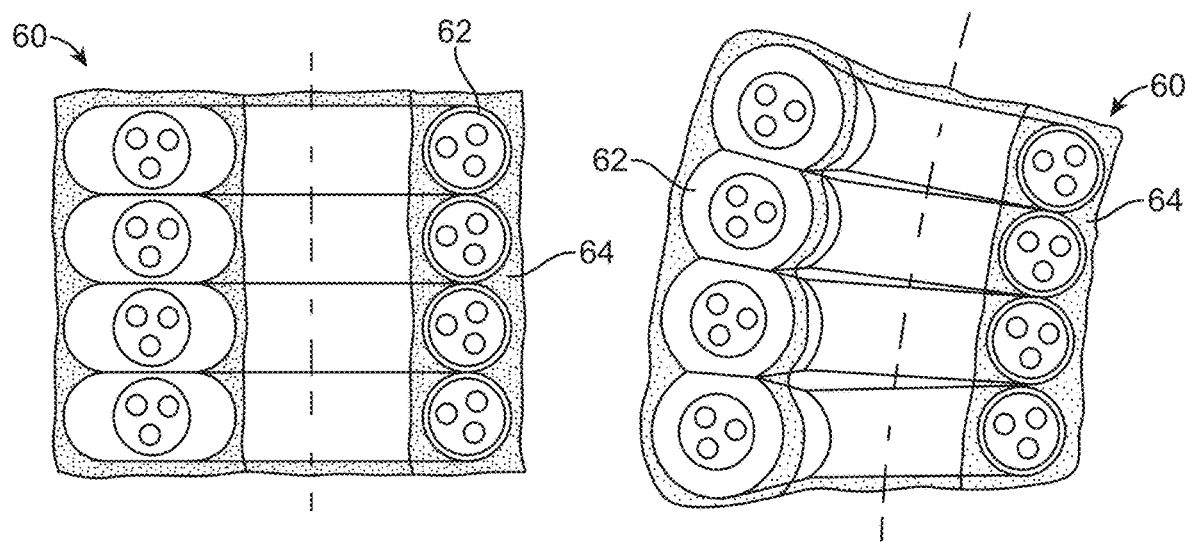
FIGS. 7A and 7B are cross-sections schematically illustrating a polymer dip coat supporting helical balloon assemblies with the balloons nominally inflated and fully inflated, respectively.

Referring now to FIGS. 7A and 7B, a simple articulated segment 60 includes a single balloon string 62 supported by a polymer matrix 64 in which the balloon string is embedded. A multilumen shaft of balloon string 62 includes 3 lumens, and the balloons of the balloon string are shown in a nominally inflated state in FIG. 7A, so that the opposed major surfaces of most of the balloons of each subset are disposed between and adjacent balloons of that subset on adjacent loops, such that pressure within the subset of balloons causes the balloons to push away from each other (see FIG. 7B). Optionally, the balloons of the subset may directly engage each other across much or all of the balloon/balloon force transmission interface, particularly when the balloons are dip-coated when in the nominally inflated state. Alternatively, a layer of matrix 64 may be disposed between some portion or all of the adjacent force-transmission balloon wall surfaces of the subset, for example, if the balloon strings are dip-coated in a deflated state (see FIGS. 8 and 9). As can be understood with reference to FIG. 7B, inflation of one or more subsets of the balloons may separate adjacent loops of the balloon string between balloons, along the tapering balloon ends, and the like. Elastic elongation of matrix 64 may accommodate some or all of this separation, or the matrix may at least locally detach from the outer surface of the balloon string to accommodate the movement. In some embodiments, localized fracturing of the polymer matrix in areas of high elongation may help to accommodate the pressure-induced articulation, with the overall bulk and shape of the relatively soft matrix material still helping to keep the balloons of the helical balloon array in the desired alignment. Bending in different orientations may optionally be induced by transmitting balloon inflation fluid through different channels of the multi-lumen shaft toward different subsets of balloons (each subset being in fluid communication via a common channel and aligned for bending in an associated lateral bending orientation, as described above). In alternative arrangements, a plurality of balloon strings can wind in parallel around axis 44, with the first string including a first subset of balloons that are aligned for bending in a first bending axis (see FIG. 6C). In such systems, the balloons may push axially (directly or indirectly, such as via the matrix) against the balloon tube 38 between balloons (see FIG. 5), rather than the balloons pushing against each other. Two, three, four, or more strings of balloons may be interleaved, with or without multi-lumen shafts, to provide the desired degrees of freedom.

Figure 8:
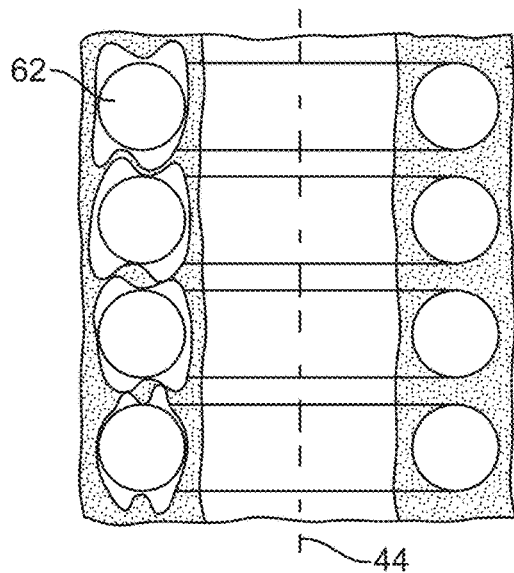
FIG. 8 is a schematic cross-sections illustrating a helical balloon assembly having fully delated balloons, and showing how balloon folding can impact efficiency of articulation.
Figure 9:
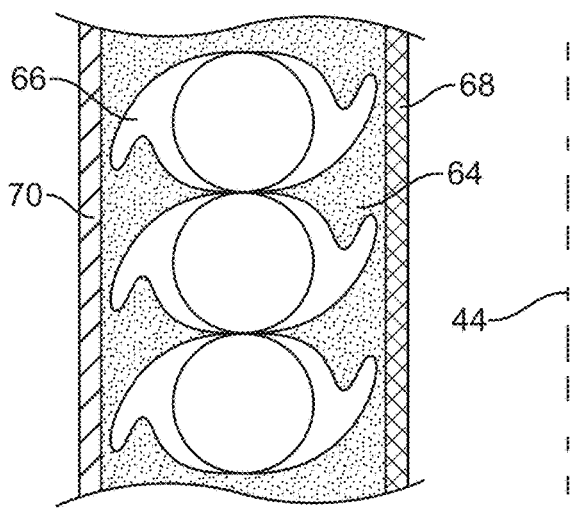
FIG. 9 is an alternative schematic cross-sections illustrating an alternative balloon folding arrangement, and showing radially inner and outer sheaths with the matrix and balloon assemblies disposed therebetween.

Referring now to FIGS. 8 and 9, shape-setting of balloon string 62 can help to improve articulation performance and uniformity along the axial length of the segment. In the embodiment of FIG. 8, the balloon have been urged toward a 4-wing "H" shaped folded balloon configuration by, for example, winding the balloon string within a helical channel of a substantially cylindrical mandrel, such as by using a threaded acme rod as the mandrel and winding the balloon string within the roughly square thread of the rod, and then heat-setting the balloons at a moderate temperature for sufficient time to maintain the balloon fold shape. In the illustrated embodiment, the major surfaces of the "H" folded shape are oriented radially; in other embodiments, the major surfaces may be oriented axially so as to increase balloon/balloon force transmission efficiency. Still other configurations may be used, including a 2-wing balloon fold configuration 66 of FIG. 9, in which the wings have been wrapped circumferentially about the multi-lumen shaft within the balloon. Other optional configurations include a 3-wing balloon fold, and any of these configurations may optionally comprise asymmetric folds, with one or more folds disposed on a radially inward portion of the balloon (relative to the helical axis) having a different amount of balloon wall material than one or more folds along a raddialy outward portion of the balloon. A vacuum may be applied to the balloons via the multi-lumen shaft as the balloons are folded, and may by maintained during shape setting and/or the embedding of the balloon in matrix 64. Local detachment of matrix 64 from an outer surface of the balloon string, and/or local fracture of the polymer matrix, adjacent the wings of the balloons during initial inflation may facilitate articulation. Note that a flexible radially inner sheath 68 and a flexible outer sheath 70 may support the segment, provide desirable inner and outer surface characteristics (such as low friction, etc.), and/or may optionally radially constrain the balloons during inflation sufficiently to enhance axial balloon expansion and the associated articulation range of motion available from each balloon of the subset.

Figure 10A:
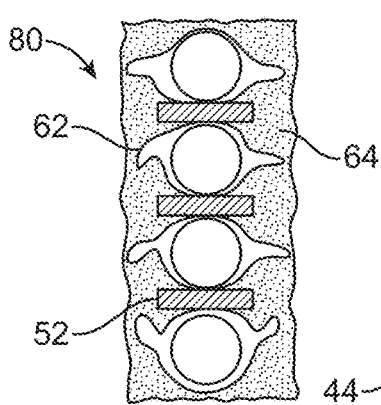
FIGS. 10A-10C are cross-sections schematically illustrating a dip-coated helical balloon assembly having a flat spring between axially adjacent balloons in an uninflated state, a nominally inflated state, and a fully inflated state, respectively, with the dip coating comprising a soft elastomeric matrix.
Figure 10B:
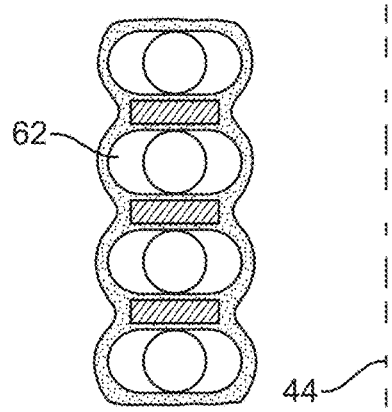
Figure 10C:
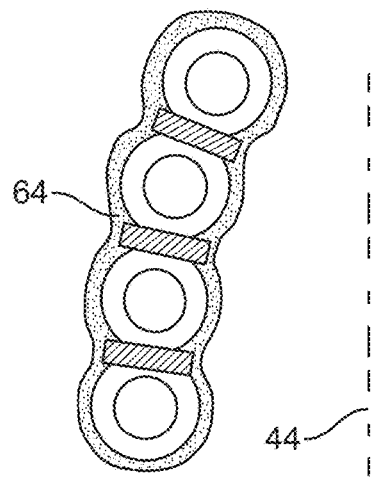

Referring now to FIGS. 10A-10C, an alternative segment 80 has a single balloon string 62 interleaved with a flat spring 52, and both the balloon string and spring are coated by an elastomeric polymer matrix 64. Shape setting of the balloons may be optionally be omitted, as axial compression of spring 52 can help induce at least rough organization of deflated balloons 62 (as shown in FIG. 10A). Local inclusion of some matrix material 64 between the balloon walls and adjacent spring surface (see FIG. 10B) may not significantly impact overall force transmission and articulation, particularly where the balloons are generally oriented with major surfaces in apposition, as the pressure force can be transmitted axially through the soft matrix material. Alternatively, the balloons may be nominally inflated during application of the matrix material, as noted above, providing a more direct balloon wall/spring interface (see FIG. 10C). As with the other embodiments of segments described herein, flexible (and often axially resilient) radially inner and/or outer sheaths may be included, with the sheaths optionally comprising a coil or braid to provide radial strength and accommodate bending and local axial elongation, such inner and/or outer sheaths often providing a barrier to inhibit release of inflation fluid from the segment should a balloon string leak.

Figure 11A:
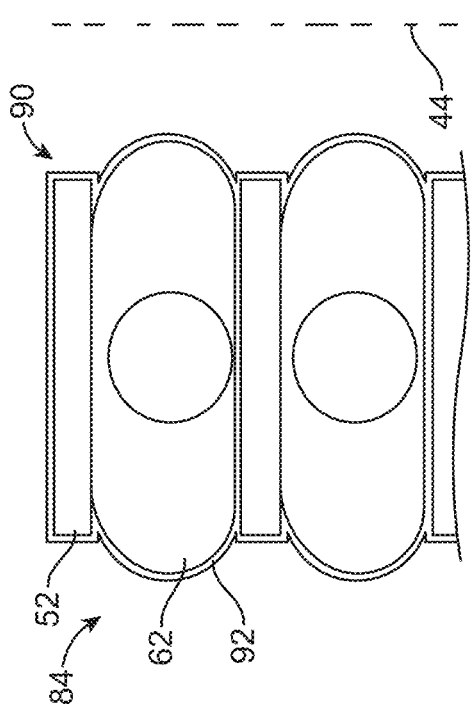
FIGS. 11A and 11B are schematically illustrations of an alternative dip-coated helical balloon assembly showing a cross-section of a flat spring sandwiched between adjacent balloons, and a cross-section of the assembly between balloons, respectively.
Figure 11B:
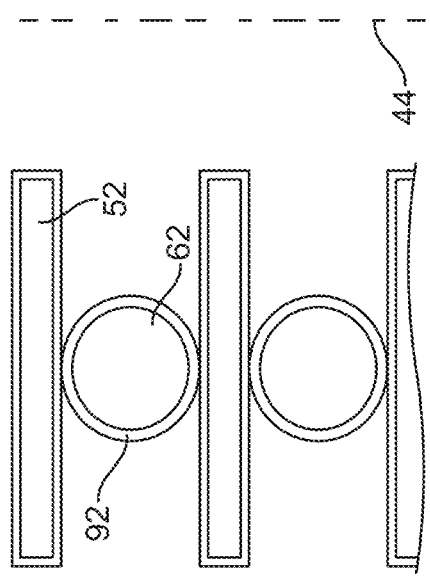

Many of the embodiments described above include soft elastomeric polymer matrices that help maintain alignment between subsets of balloons in an articulation balloon array, with the matrix optionally filling spaces between balloons. Referring now to FIGS. 11A and 11B, an alternative segment 90 includes a polymer matrix layer 92 that may be quite thin, typically being less than a half millimeter, often being 0.25 mm thick or less in at least some areas, and which flexibly adheres the balloons of the balloon string in the desired alignment without filling the spaces between balloons or the like. Matrix layer 92 may again comprise an elastomeric polymer, but may have a significantly higher hardness than the soft, space-filling matrices described above. The articulation performance of segment 90 may benefit from coating of balloon string 62 and spring 52 while the balloons are in nominally inflated state (with detachment of polymer matrix from the balloon string and/or localized failure of the matrix between the small-profile region of string 62 and spring, as can be understood with reference to FIG. 11B) facilitates initial articulation. Alternatively, the balloon may be in a partially or fully inflated state when the matrix is applied so that the coating on the balloon string between balloons and coating on the spring surfaces are separate, as can also be understood with reference to FIG. 11B.

Figure 12:
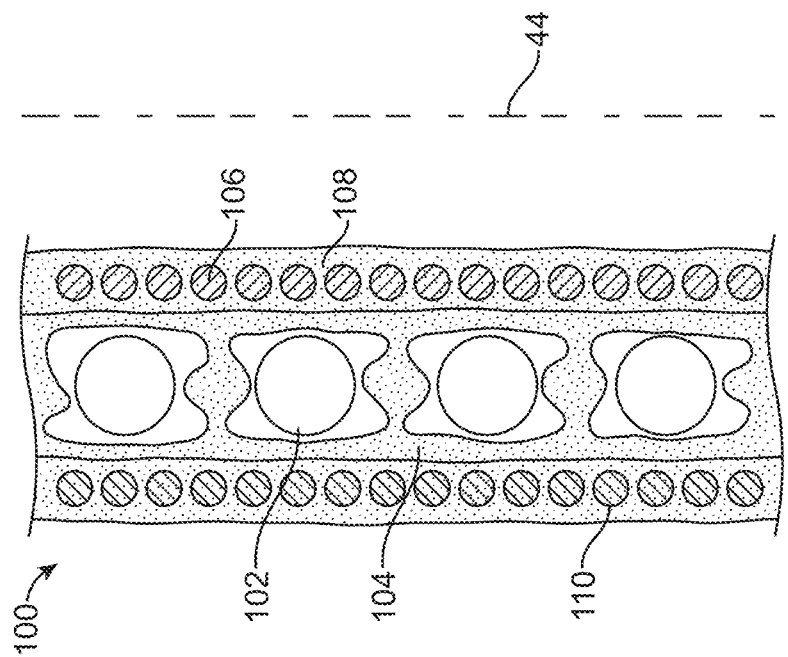
FIG. 12 is a cross-section schematically illustrating yet another alternative dip-coated helical balloon assembly embedded within a relatively soft polymer matrix, with support coils disposed radially inward and outward of the balloon assemblies and dip-coated in a different, relatively hard polymer matrix.

Referring now to FIG. 12, an exemplary segment 100 was fabricated with an intermediate sub-assembly including balloon string 102 embedded in an intermediate matrix 104. An inner sheath is formed radially inward of (and optionally prior to the assembly of) the intermediate sub-assembly by embedding an inner spring 106 within an inner matrix 108. An outer sheath is formed radially outward of (and optionally after assembly of) the intermediate assembly, with the outer sheath including an outer spring 110 and an outer matrix. Segment fabrication parameters and characteristics are summarized in Table 1.

TABLE 1

Fabrication processing parameters and characteristics

| Characteristic/Parameter | Condition | Comment |
|---|---|---|
| Inside Spring | | |
| Wire Material | 304V SS Spring Temper Wire | |
| Wire Diameter | 0.014" | |
| ID | 0.140" | |
| OD | 0.168" | |
| Pitch | 0.045 | measure gap (target = .031") spacing with gage pin |
| Wind Direction | Right Hand | |
| Outside Spring | | |
| Wire Material | 304V SS Spring Temper Wire | |
| Wire Diameter | 0.014" | |
| ID | 0.245" | |
| OD | 0.273" | |
| Pitch | 0.045 | |
| Wind Direction | Right Hand | |
| Spring Constant—k | TBD | |
| Balloon Coil (Middle) | | |
| Tube Material | Pebax 63D | |
| Tube ID | 0.016" | |
| Tube OD | 0.026" | |
| Balloon Spacing | TBD | measurement of proximal end of 1 balloon to the proximal end of next balloon |
| Inflation Pressure (Hot air station) | 90 psi | |
| Balloon Mold Diameter | 0.075" | |
| Number of Balloons | 5 | |
| Nitinol Coring Wire Diameter | 0.014" | wire used during balloon wind shape set |

TABLE 1-continued

Fabrication processing parameters and characteristics

| Characteristic/ Parameter | Condition | Comment |
|---|---|---|
| Shape Setting Spring Specifications | Gap between coils—0.046"; Pitch—0.084"; Wire Diameter—0.038"; Wind Direction—Left Hand | Tool used for balloon chambers flattening mitigation during shape set processing |
| Wind Shape Set Temperature | 100 Celsius | |
| Wind Shape Set Time | TBD | |
| Wind Direction | Left Hand | |
| Balloons per Revolution | 1 | |
| Inflation Multi-lumen Shaft Included Inside, Middle and Outside Silicone Layers | No | |
| Type | Dragon Skin 10 Medium | |
| Manufacturer | Smooth-On, Inc. | |
| Durometer | 10 Shore A | |
| Viscosity | 23,000 cps | |
| Elongation at Break % | 1000% | |
| Pot Life | 20 minutes | |
| Cure Time @ ambient | 5 hours | |
| Dip Withdraw Rate | 0.5 in/min | |
| Wall Thickness | ~0.009" | |

Measurements of the assembled components are provided in Table 2.

TABLE 2

Prototype measurements

| Layers of Prototype from ID to OD | | Actual OD (in) |
|---|---|---|
| 1 | Inside Spring | 0.168 |
| 2 | Inside Silicone | ~0.186 |
| 3 | Balloon Coil | ~0.220 |
| 4 | Middle Silicone | 0.240 |
| 5 | Outside Spring | 0.272 |
| 6 | Outside Silicone | 0.290 |
| | ID of Prototype | 0.140 |

Note that as in this embodiment, it will often be beneficial for any inner or outer spring to be counterwound relative to the balloon string. First, when the loops of the springs cross the balloons it may help inhibit radial protrusion of the balloons through the coils. Second, it may help to counteract rotational unwinding of the balloon coil structure with balloon inflation, and thereby inhibit non-planar articulation of the segment form inflation of a single balloon subset. Alternative embodiments may benefit from harder matrix materials encompassing the inner or outer springs (or both), from replacing the inner or outer springs (or both) with a braid, multiple layers of threads, fine wire or polymer lines, eliminating the springs altogether, or the like.

Referring now to FIGS. 13A-14E, alternative segment structures include opposed balloons disposed within channels of segment frames or skeletons to locally axially elongate or contract the frame, thereby laterally bending the frame or changing the axial length of the frame. Referring first to FIG. 13A, a schematically illustrated frame structure 120 includes an axially interleaved set of frame members, with an inner frame 122 having a radially outwardly open channel, and an outer frame 124 having a radially inwardly open channel. The channels are both axially bordered by flanges, and radially bordered (at an inner or outer border of the channel) by a wall extending along the axis. A flange of the inner frame extends into the channel of the outer frame, and a flange of the outer frame extends into the channel of the inner frame. Axial extension balloons 126 can be placed between adjacent flanges of two inner frames or between flanges of two adjacent outer frames; axial retraction balloons 128 can be placed between a flange of an inner frame and an adjacent flange of an outer frame. As more fully explained in US Patent Publication No. US20160279388, entitled "Articulation Systems, Devices, and Methods for Catheters and Other Uses," published on Sep. 29, 2016 (assigned to the assignee of the subject application and the full disclosure of which is incorporated herein by reference), inflation of a subset of extension balloons 126 along one side of the frame locally extends the axial length of the frame and can bend the frame away from the balloons of the subset. A subset of retraction balloons 128 is mounted in opposition to that local extension, so that inflation of those retraction balloons (with concurrent deflation of the extension balloons) may move the flanges between the balloons in the opposed direction, locally decreasing the length of the frame and bending the axis of the frame toward the inflating retraction balloons. As can be understood with reference to FIGS. 13B-13E, annular frame segments 120' may have an axially series of ring-shaped inner and outer frames defining the flanges and channels. As shown in FIGS. 14A-14E, helical versions of the frame system may have helical inner and outer frame members 122', 124', with extension balloons 126 and retraction balloons 128 being disposed on multiple helical balloon strings extending along the helical channels.

Figure 15:
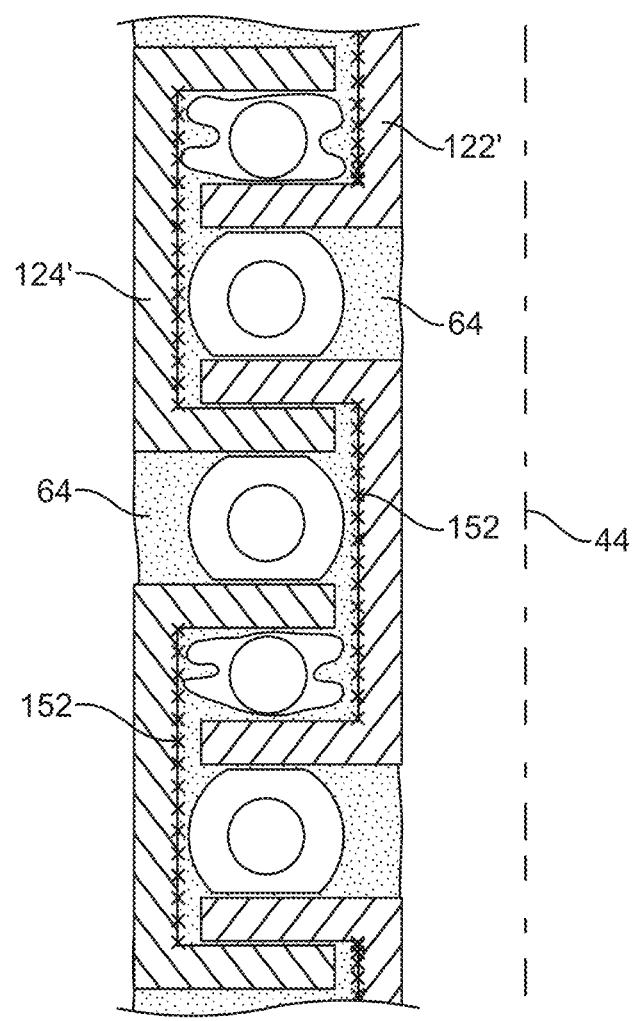
FIG. 15 is a cross-section schematically illustrating an elongation-contraction frame similar to those of FIGS. 13A-14E, showing a soft elastomeric polymer matrix supporting balloon assemblies within the frames.

Referring now to FIG. 15, embedding the balloons within the helical frames 122', 124' or ring frames described herein within polymer matrix 64 may help maintain alignment of the subsets of balloons despite frame articulation. Articulation performance may be enhanced by the use of soft matrices (with Shore A durometers of 2 to 15), and by inhibiting adhesion at the frame/matrix interface 152 between the axial wall of the frames and the matrix in the channels. Preferably, a slippery interface 152 is provided by a low-friction surface in the channels of the frames between flanges, such as by coating the axial walls with a mold release agent, a PTFE polymer coating or frame material, or the like. Local friction inhibition between the matrix and the axial wall may be provided by forming the frames from a low-friction polymer (such as PTFE or the like) and selectively enhancing adhesion along the surfaces of the flanges using chemical etching, plasma etching, apertures through the flanges, surface features or roughening along the flanges, or the like.

Referring now to FIGS. 16A-16C, still further alternative structures 162, 172 can make use of an elastomeric polymer matrix over one or more balloons on a balloon string to provide controlled articulation. In the embodiment of FIG. 16A, balloon 164 is deflated and two wings 166 of the deflated balloon are folded around a multilumen shaft. At least a portion of the deflated balloon is first coated with a thin, low strength layer 168, with the coated portion including the region around the folded wings. A second layer 170 is disposed over the balloon and the first layer, with the send layer being elastomeric and having sufficient elongation to allow inflation of the balloon from the folded configuration of FIG. 16A to the inflated configuration of FIG. 16C. As described above, the low-strength polymer matrix material of first layer 168 may detach from the underlying balloon wall, and/or may fracture locally. This facilitates resilient distention of sufficiently large surface regions of the outer balloon to accommodate movement of the wings and balloon diameter growth, while allowing the outer layer to resiliently contract when inflation fluid flows out of the balloon. An alternative four wing H fold configuration of the balloon is shown in FIG. 16 B. Local voids in the first layer adjacent major surfaces 174 of the balloon may provide a more rigid balloon force transmission interface. Exemplary embodiments may employ low strength, low durometer polymer materials such as soft silicone polymers for first layer 168, and higher strength, high-elongation silicone polymers for second layer 172. Other embodiments may make use of an inner release agent and a silicone, polyurethane, or other elastomer over the release agent. Optionally, the balloons may be folded and coated while the balloon strings remain in a relatively straight configuration (i.e., prior to forming the balloon assembly into a helix). The total coating thickness over the individual balloons, if coated prior to assembly with other components of a segment, will often be less than 0.010", preferably being less than 0.004".

Figure 17:
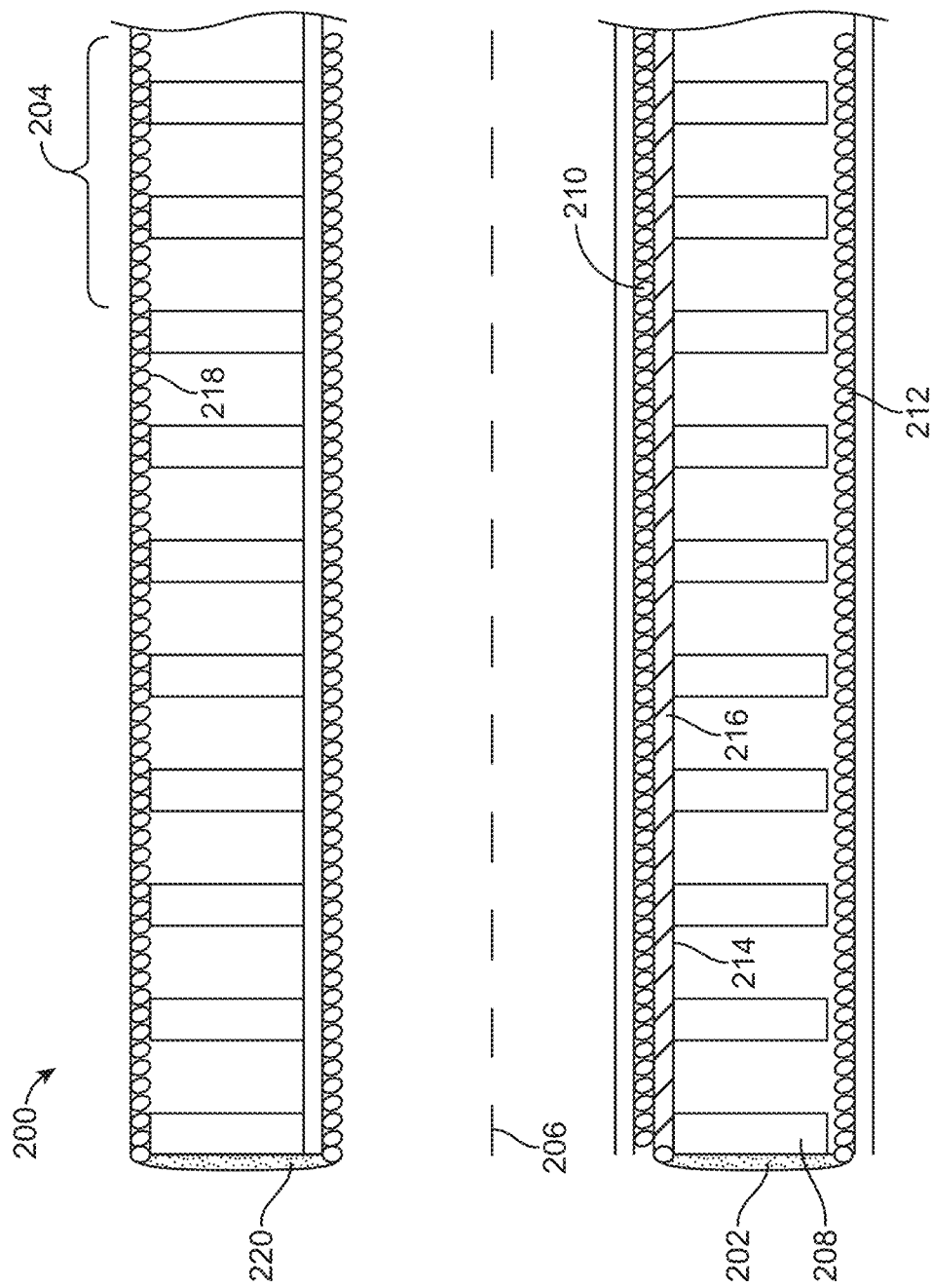
FIG. 17 schematically illustrate a simplified cross-section of a helical frame within an annular space bordered by an inner reinforced polymer sheath and an outer reinforced polymer sheath, in which a proximal portion of one or both sheath(s) can slide axialy relative to a balloon array within the annular space to facilitate articulation.

Referring now to FIG. 17, an alternative articulated assembly 200 has many of the components described above, including a helical balloon array similar to that of FIG. 5. Assembly 200 has a distal end 202 and a proximal portion 204, with the assembly being disposed along a segment of axis 206 so as to allow the user to selectively bend and elongate the segment by directing inflation fluid toward subsets of balloons within a helical balloon array (see FIG. 5; not shown in FIG. 17). The helically balloon array and associated fluid channels are wound between loops of a flat helical spring coil 208. In assembly 200, the balloon array and flat spring have an annular cross section (extending around axis 206) and are disposed within an annular space bordered by an inner sheath 210 and an outer sheath 212.

As they extend along the articulated portion of the catheter (and may extend proximally or distally beyond the articulated portion, the inner and outer sheath structures will generally have sufficient lateral flexibility to accommodate the desired lateral bending and/or axial elongation of the fluid-driven segment. Additionally, the inner and outer sheaths can be configured to serve some or all of the following functions: inhibiting radial migration of the balloons; inhibiting embolization of any inflation fluid (gas or liquid) that may inadvertently be released from the balloon array; providing a smooth, low friction, and/or lubricious outer surface of the catheter (to facilitate movement of the catheter through surrounding tissues or a surrounding outer guide catheter) or inner surface (to facilitate movement of guidewires and tools relative to the lumen of the inner sheath) or both; enhancing a bending stiffness of at least the articulated segment or portion of the catheter, and the like. To provide the desired combinations of capabilities, each of these sheaths may benefit from a reinforced polymer matrix structure having a combination of materials. Additionally, the overall capabilities of the articulated structure can benefit from configuring the interfacing surfaces so as to allow relative axial motion between one or both of the sheaths and the balloon array and flat helical spring 208. For example, inner sheath 210 may have an inner balloon-restraining surface 214 defined by a polymer layer 216. Inner balloon-restraining surface 214 may be generally smooth, and layer 216 may help limit axial sliding friction against the components contained within the annular space between the sheaths. An inner surface 218 of outer sheath 210 may similarly be configured to accommodate sliding against the balloon array and/or helical spring 208. To maintain overall structural integrity of the articulated portion, inner and outer sheaths 210, 212 may be axially affixed relative to the balloon array and spring 208 adjacent distal end 202 by adhesive 220. However, to accommodate axial elongation and bending, proximal portion 204 (proximal of the distal end) the balloon array and spring 208 may slide axially against one or both of the sheaths 210, 212. Note that the adjacent radial surface(s) of spring 208 can be provided with a smooth and/or low friction surface to facilitate this axial sliding, such as by coating the spring with a low-friction material such as parylene, PTFE, or the like. The adjacent radial surface(s) of balloon array may optionally also benefit from a low-friction material, even if the engaging axial surfaces of the spring and array are configured to inhibit relative circumferential and/or radial movement (such as being bonded or embedded together in a polymer matrix as described above).

Regarding the structure of inner sheath 210, a high hoop-strength reinforcing material such as metal or relatively rigid polymer filament can be included, often in the form of a coil or braid. A coil of stainless wire having a diameter from 0.004" to 0.014" can optionally be used with a closed or near-closed pitch. Axial sliding surface 214 will typically be radially outward of the reinforcing material, and the underlying layer 216 may comprise an elastomeric polymer such as PEBAX™ PEBA polymer tube having a hardness in a range from 30D to 60D, an ID of 0.100" to 0.150", and a wall thickness of 0.004" to 0.015", with the layer being urged radially outwardly by the coil therein. Optionally, an inner polymer layer (not shown) is disposed radially within the reinforcing material, and the layers may be fused or bonded together. Low friction coatings (such as PTFE) or lubricious layers (such as commercially available hydrophilic or hydrophobic coatings) may be applied to the inner and/or outer surfaces, with the preferred reinforced matrix materials being very flexible, smooth, and atraumatic. The structure of outer sheath 212 may have many of the properties and structures described above regarding the inner sheath 210, though the sheaths will often have differing composite structures due to the differing loads and strains as the articulated portion of the catheter bends and elongates, and to provide the desired catheter characteristics (pushability, trackability, and crossability) for manual advancement toward the target tissue. The exemplary outer coil 212 includes a stainless coil formed of stainless wire having a pitch and diameter in the ranges described above regarding sheath 210, and a polymer coating of a polymer having a high-elongation (preferably 300% or more) and low durometer (preferably 60 A or less, optionally 30 A or less, ideally being 10 A) such as a silicone or urethane. Note that the coils are preferably both counterwound relative to the balloon array, and that the reinforcing materials may comprise flat ribbons, braids, and smaller radial dimensions when fused between inner and outer polymers.

While the exemplary embodiments have been described in some detail for clarity of understanding and by way of example, a variety of modifications, changes, and adaptations of the structures and methods described herein will be obvious to those of skill in the art. For example, while articulated structures may optionally have tension members in the form of pull-wires as described above, alternative tension members in the form of axially slidable tubes in a coaxial arrangement may also be employed. Hence, the scope of the present invention is limited solely by the claims attached hereto.

What is claimed is:

1. An elongate articulatable body comprising:
a first balloon string including:
an inflation tube having a first end and a second end with a first lumen extending therebetween; and
a first set of balloons distributed along the inflation tube, the first set of balloons in communication with the first lumen;
the first balloon string comprising a helical balloon coil having a helical axis with the first set of balloons being offset from the helical axis along a first lateral bending axis; and
a first polymer matrix disposed on the first balloon string so as to help maintain alignment between the first set of balloons when inflation fluid is transmitted through the first lumen and the first set of balloons bend the helical axis laterally;
wherein the first balloon string is wound with a first orientation, wherein a spring is radially offset from the first balloon string and is wound with a second orientation opposed to the first orientation so that loops of the spring cross loops of the first balloon string, and wherein the loops of the spring radially restrain radial expansion of the first set of balloons so as to enhance axial elongation of the first balloon string during inflation so as to increase lateral bending articulation.

2. The elongate articulatable body of claim 1, wherein the first polymer matrix comprises an elastomeric polymer coating over the first balloon string.

3. The elongate articulatable body of claim 1, wherein the first set of balloons and the inflation tube are embedded in the first polymer matrix.

4. The elongate articulatable body of claim 1, wherein the first polymer matrix comprises a first silicone.

5. The elongate articulatable body of claim 1, wherein the first polymer matrix comprises one or more of a latex, a polyisoprene, a urethane, a polyurethane, a polyether block amide, a thermoplastic, a thermoplastic elastomer, and/or a nitrile.

6. The elongate articulatable body of claim 1, wherein the first polymer matrix has a durometer hardness of less than 20A.

7. The elongate articulatable body of claim 1, wherein the helical balloon coil defines a plurality of circumferential loops, each balloon of the first set of balloons being disposed on an associated loop, wherein the first polymer matrix is contiguous between the loops of the spring.

8. The elongate articulatable body of claim 1, wherein the helical balloon coil defines a plurality of circumferential loops, each balloon of the first set of balloons being disposed on an associated loop of the plurality of circumferential loops, wherein the elongate articulatable body includes at least one additional helical body having a plurality of other loops, wherein the first polymer matrix couples the plurality of circumferential loops of the helical balloon coil to adjacent the plurality of other loops of the at least one additional helical body.

9. The elongate articulatable body of claim 1, further comprising a second polymer matrix disposed over the first polymer matrix, the second polymer matrix having a durometer greater than that of the first polymer matrix.

10. An elongate articulatable body comprising:
a first balloon string including:
an inflation tube having a first end and a second end with a first lumen extending therebetween; and
a first set of balloons distributed along the inflation tube, the first set of balloons in communication with the first lumen;
the first balloon string comprising a helical balloon coil having a helical axis with the first set of balloons being offset from the helical axis along a first lateral bending axis;
a first polymer matrix disposed on the first balloon string so as to help maintain alignment between the first set of balloons when inflation fluid is transmitted through the first lumen and the first set of balloons bend the helical axis laterally; and
a first spring supporting the helical balloon coil so as to bias the helical axis toward a straight configuration and/or to urge the first set of balloons from a fully inflated state, wherein the first polymer matrix helps to couple the first spring to the helical balloon coil.

11. The elongate articulatable body of claim 10, wherein the first spring is disposed radially inward of the helical balloon coil or radial outward of the helical balloon coil.

12. The elongate articulatable body of claim 11, wherein the helical balloon coil is disposed radially between the first spring and a second spring.

13. The elongate articulatable body of claim 12, further comprising a second polymer matrix disposed over the first polymer matrix, the second polymer matrix comprising an elastomeric coating encompassing at least one of the first spring and/or the second spring.

14. The elongate articulatable body of claim 13, wherein the second polymer matrix comprises a material that is the same as a material of the first polymer matrix, the second polymer matrix being adhered to the first polymer matrix.

15. The elongate articulatable body of claim 10, wherein the first spring is disposed axially between loops of the helical balloon coil.

16. The elongate articulatable body of claim 15, wherein the first spring comprises spring member with flat a cross-section having an axial thickness and a radial width greater than the axial thickness.

17. The elongate articulatable body of claim 16, wherein the first spring comprises a machined spring.

18. The elongate articulatable body of claim 17, wherein the first spring has a plurality of spring members.

* * * * *